United States Patent
Kent et al.

(10) Patent No.: US 9,239,048 B2
(45) Date of Patent: Jan. 19, 2016

(54) PUMP FOR STERILISATION APPARATUS

(75) Inventors: Barry Kent, Havelock North (NZ);
Jeremy Peter Turner, Omorokoa (NZ)

(73) Assignee: TRISTEL PLC, Snailwell, Cambridgeshire (GB)

( * ) Notice: Subject to any disclaimer, the term of this patent is extended or adjusted under 35 U.S.C. 154(b) by 290 days.

(21) Appl. No.: 13/985,394

(22) PCT Filed: Jan. 31, 2012

(86) PCT No.: PCT/EP2012/051594
§ 371 (c)(1),
(2), (4) Date: Aug. 14, 2013

(87) PCT Pub. No.: WO2012/110313
PCT Pub. Date: Aug. 23, 2012

(65) Prior Publication Data
US 2014/0010675 A1    Jan. 9, 2014

(30) Foreign Application Priority Data
Feb. 15, 2011 (GB) .................. 1102609.3

(51) Int. Cl.
*F04B 43/12* (2006.01)
*F04B 43/00* (2006.01)
(Continued)

(52) U.S. Cl.
CPC ........... *F04B 43/009* (2013.01); *F04B 43/0081* (2013.01); *F04B 43/12* (2013.01);
(Continued)

(58) Field of Classification Search
CPC .. F04B 43/0081; F04B 43/12; F04B 43/1253; F04B 43/009; A61L 2202/15; A61L 2/18; A61L 2202/24; A61L 2019/343
See application file for complete search history.

(56) References Cited

U.S. PATENT DOCUMENTS 3,404,335 A * 10/1968 Kidder .......................... 324/445
3,554,674 A    1/1971 Huret
(Continued)

FOREIGN PATENT DOCUMENTS

DE    100 50 182    11/2001
EP    0 745 400    12/1996
(Continued)

OTHER PUBLICATIONS

International Search Report from International Application No. PCT/EP2012/051594 mailed Jun. 6, 2012.
(Continued)

*Primary Examiner* — Bryan Lettman
(74) *Attorney, Agent, or Firm* — Merchant & Gould P.C.

(57) ABSTRACT

A peristaltic pump (2) for use in a sterilization apparatus (10) comprises: a flexible pump hose (44) having an outlet end and an inlet end, and an electrically conductive fitting (53) at each end; a motor-driven impeller (46) disposed in relation to the pump hose (44) such that when the impeller (46) is driven it will intermittently bear against the pump hose (44) so as to bring the internal walls of the pump hose together (62); a first electrode (52a) in contact with the conductive fitting (53a) at the outlet end of the pump hose (44), and a second electrode (52b) in contact with the conductive fitting (53b) at the inlet end of the pump hose (44); means (70) for applying a voltage across the first and second electrodes (52); and means (70) for measuring an electrical property between the conductive fittings (53). Other aspects of the invention provide a sterilization apparatus including the pump, and a method of using the sterilization apparatus.

15 Claims, 18 Drawing Sheets

(51) Int. Cl.
 *A61B 19/00* (2006.01)
 *A61L 2/18* (2006.01)

(52) U.S. Cl.
 CPC ......... *F04B43/1238* (2013.01); *F04B 43/1253* (2013.01); *F04B 43/1261* (2013.01); *A61B 2019/343* (2013.01); *A61L 2/18* (2013.01); *A61L 2202/15* (2013.01); *A61L 2202/24* (2013.01)

(56) References Cited

U.S. PATENT DOCUMENTS

| | | | |
|---|---|---|---|
| 4,138,639 A | | 2/1979 | Hutchins |
| 4,232,828 A | | 11/1980 | Shelly, Jr. |
| 5,470,211 A | * | 11/1995 | Knott et al. ............... 417/477.9 |
| 5,657,000 A | * | 8/1997 | Ellingboe ................... 340/608 |
| 6,558,620 B1 | * | 5/2003 | Sanford et al. ............... 422/28 |
| 6,585,943 B1 | * | 7/2003 | Sanford et al. .............. 422/307 |
| 6,814,932 B2 | * | 11/2004 | Hlebovy et al. ............... 422/28 |
| 2004/0265154 A1 | * | 12/2004 | McDowell et al. ........... 417/474 |
| 2006/0269442 A1 | | 11/2006 | Nguyen et al. |
| 2007/0260111 A1 | | 11/2007 | Baur |
| 2008/0115814 A1 | * | 5/2008 | Hasegawa et al. .......... 134/56 R |
| 2008/0267812 A1 | * | 10/2008 | Kawachi et al. ................. 422/3 |
| 2009/0158539 A1 | * | 6/2009 | Onishi et al. ............. 15/104.066 |
| 2010/0313996 A1 | | 12/2010 | Breault et al. |

FOREIGN PATENT DOCUMENTS

| | | |
|---|---|---|
| EP | 1 184 071 | 3/2002 |
| EP | 2 080 486 | 7/2009 |
| FR | 2 520 639 | 8/1983 |
| RU | 2351275 C2 | 4/2009 |
| WO | WO 2008/020770 | 2/2008 |
| WO | WO 2010/125366 | 11/2010 |

OTHER PUBLICATIONS

International Preliminary Report on Patentability from International Application No. PCT/EP2012/051594 mailed May 29, 2013.

* cited by examiner

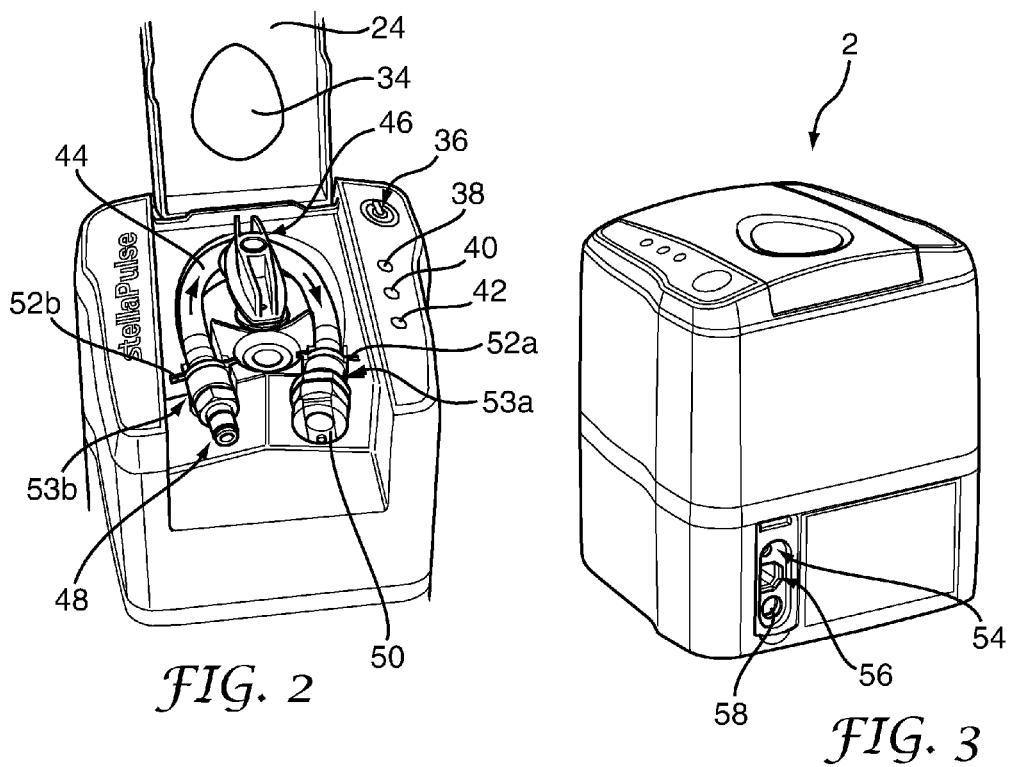
FIG. 2
FIG. 3
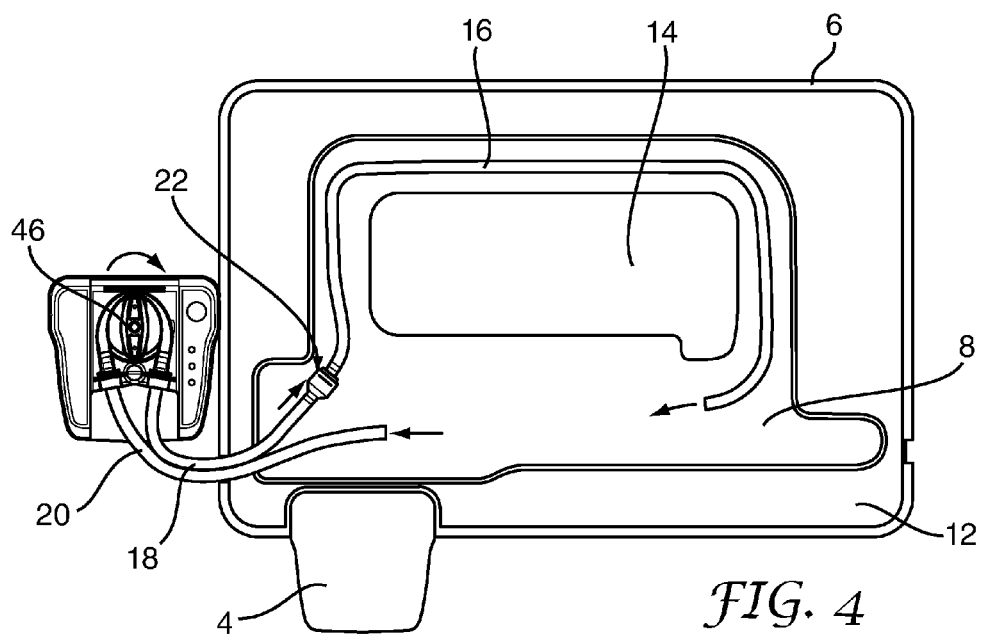
FIG. 4

Fluid Signal

X - Y = Electrical current source

Waveform if Pre-cycle peaks counted

Outlet Tube Length

Fluid sensor waveform and threshold levels ial, provided with electrically conductive fittings or couplings 53 at each end. In this embodiment, the fittings 53 are made of stainless steel and include conductive hose barbs

PUMP FOR STERILISATION APPARATUS

This application is a National Stage Application of PCT/EP2012/051594, filed 31 Jan. 2012, which claims benefit of Ser. No. 1102609.3, filed 15 Feb. 2011 in Great Britain and which applications are incorporated herein by reference. To the extent appropriate, a claim of priority is made to each of the above disclosed applications.

The present invention relates to a pump for a sterilisation apparatus, sterilisation apparatus including the pump, and a method of use of the apparatus. The apparatus is particularly for use in sterilising medical instruments such as endoscopes.

Endoscopes must be thoroughly cleaned and sterilised after use on one patient, before use on another patient. A number of washer-disinfectors are known for carrying out such cleaning and sterilising procedures.

WO 2008/020770 discloses sterilisation apparatus which includes a tray for receiving an item to be sterilised, and a drain having a valve which is operated by an electronic controller. The controller is configured to operate opening and closing of the drain valve to control exposure time of equipment to sterilisation fluid in the tray. The controller can also keep a log of various parameters relating to sterilisation cycles, including sterilisation times and dates, and details of equipment and operators.

For endoscopes which have a lumen, ie, an internal cavity running along the length of the endoscope, the apparatus may include a pump for pumping sterilising fluid into one end of the lumen, through the endoscope, and out the other end so as to sterilise internal surfaces in addition to external surfaces. Insufficient sterilisation may result if the lumen is blocked, or if the pump fails to cycle the sterilising fluid through the lumen for any other reason.

SUMMARY OF THE INVENTION

Aspects of the invention are specified in the independent claims. Preferred features are specified in the dependent claims.

The invention provides a pump that enables a sterilisation process to be carried out correctly unsupervised, so that sterilised medical instruments are not damaged and are fully sterilised safe for use, or which will signal an error condition in the event of a blockage or other malfunction.

In prior art peristaltic pumps, at least one roller is always pinching the pump hose, and at the mid-point of the rotor's rotation the pump hose is pinched at two places. In an embodiment of the present invention, there is at least one point during the rotation of the rotor when the pump hose is not substantially pinched so that a fluid path exists through the pump hose from the inlet end to the outlet end.

Examples of prior art peristaltic pumps are described in EP 0 745 400 and US 2004/0265154.

BRIEF DESCRIPTION OF THE DRAWINGS

The invention will now be further described, by way of example only, with reference to the following drawings in which:

FIG. 2 is a front view of the pump shown in FIG. 1, with lid open;

FIG. 3 is a rear view of the pump of FIG. 2 with lid closed;

FIG. 4 is a top view of the apparatus of FIG. 1 with the pump lid open;

DETAILED DESCRIPTION

Figure 1:
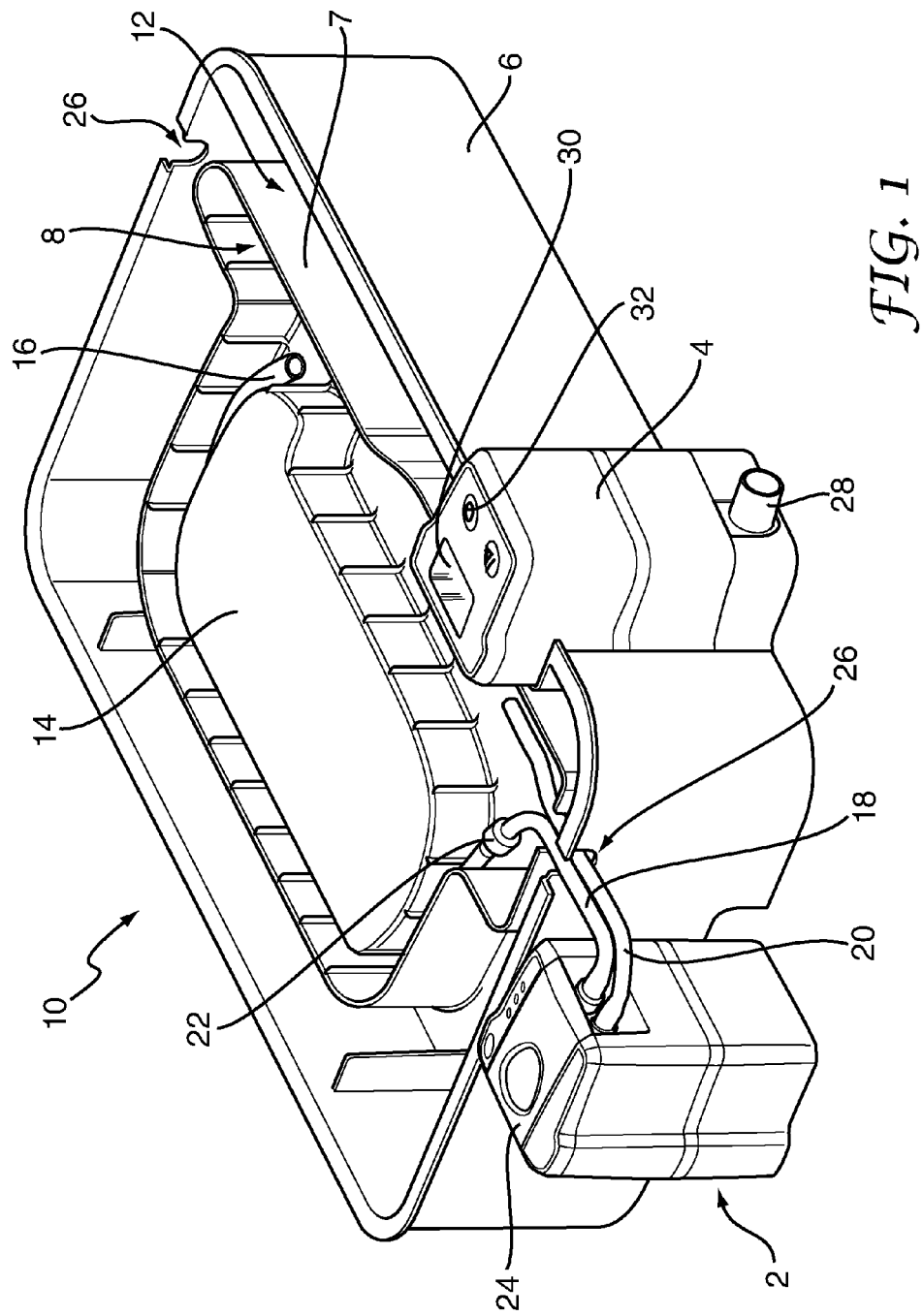
FIG. 1 shows apparatus in accordance with an embodiment of the invention.

Sterilisation apparatus 10, shown in FIG. 1, comprises a tray 6, an electronic controller 4 and a peristaltic pump 2. The tray 6 and details of the operation of the controller 4 are described in WO 2008/020770. In addition to the features of the prior art controller, the present controller is configured to control the pump 2 and receive data from it.

The tray 6 includes a sterilisation compartment 8 defined between an inner wall 7 and an island 14. In use, the sterilisation compartment 8 receives an item to be sterilised, for example an endoscope 16. The sterilisation compartment 8 is surrounded by an overflow compartment 12 which enables the sterilisation compartment 8 to be completely filled with sterilising fluid without the fluid spilling out of the tray 6. The sterilisation compartment 8 is connected to a drain outlet 28 via a valve (not shown) in the controller (4), which can be programmed to operate the valve after a pre-set time to allow drainage of sterilising fluid from the sterilisation compartment. The controller 4 has program buttons 32 to input instructions and a display 30 for displaying information about the sterilisation process or prompting user input.

The pump 2 has a lid 24, an outlet hose 18 and an inlet hose 20. The term 'hose set' will be used herein to refer to the outlet hose 18, inlet hose 20 and any associated fittings or couplings. In this example, the outlet hose 18 is connected to an endoscope 16 via a connector 22. The endoscope 16 has a central lumen, and there is an open fluid path between the outlet hose 18 and the lumen of the endoscope 16. The outlet hose 18 and inlet hose 20 are disposed through a cable opening 26 in an external wall of the tray 6. The free end of the inlet hose 20 lies on or adjacent to the bottom of the sterilisation compartment 8, so that, in use, sterilising fluid will be drawn into the inlet hose 20 by operation of the pump 2, while fluid is pumped through the lumen of the endoscope 16. Each of the outlet hose 18 and inlet hose 20 may optionally be provided with a filter (not shown) to remove particulates from the circulating fluid.

Referring now to FIG. 2, the pump 2 includes a pump hose 44, in this example made of a flexible silicone rubber matewhich are a push-fit for the ends of the pump hose. The fitting 53a at the outlet end of the pump hose 44 is provided with a female connector 50 and the fitting 53b at the inlet end of the pump hose 44 is provided with a male connector 48. The connectors 50, 48 are connected, respectively, to the outlet hose 18 and the inlet hose 20. The conductive fitting 53a at the outlet end of the hose pump 44 is in electrical contact with a first electrode contact clip 52a, and the conductive fitting 53b at the inlet end of the hose pump 44 is in electrical contact with a second electrode contact clip 52b. It will be understood that it is not necessary that the conductive part of the fitting be in direct contact with the end of the hose. Providing that the conductive part is in contact with fluid passing through the hose, it could be located within or on a non-conductive part of the fitting which is fitted to the hose.

A motor-driven impeller 46, which in this example is a rotor ('pump roller'), is disposed in relation to the pump hose 44 such that when it is driven it will intermittently bear against the pump hose 44 at at least one point so as to bring the internal walls of the pump hose together, as will be described in more detail with reference to FIGS. 5 and 6.

The pump 2 may have one or more control buttons and one or more display means for conveying information about the state of the pump. In this embodiment, the pump 2 has a standby button 36, a power LED 38, a Bluetooth LED 40, and a pump/fault LED 42. This embodiment of the pump 2 also includes (FIG. 3) a reset switch 54, a USB socket 56 for firmware updates, and a power jack 58.

As shown in FIG. 4, clockwise rotation of the impeller 46 drives fluid out of the pump hose 44 through the outlet hose 18 and the lumen of the endoscope 16 in the sterilisation compartment 8. At the same time, fluid is drawn into the free end of the inlet hose 20 and through the pump hose 44.

Figure 5:
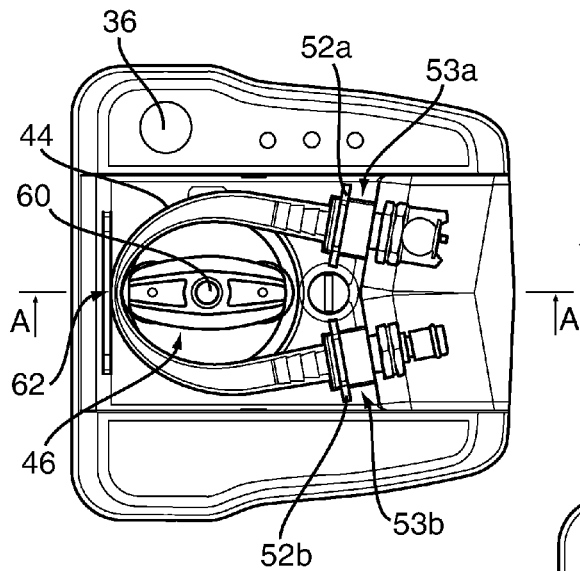
FIGS. 5 and 6 are top views of the pump of FIG. 2 at different stages of the pumping process.
Figure 6:
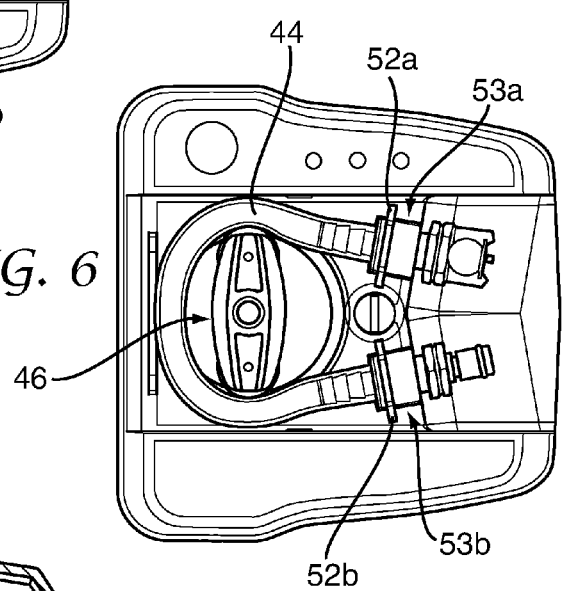

Referring now to FIG. 5, when the impeller 46 is turned about its spindle 60 it intermittently bears against the pump hose 44 at a pressure point 62 so as to bring together the internal walls of the pump hose. In a preferred embodiment, the internal walls are brought together so as to form a substantially fluid-tight seal. It will be understood that it is not essential that intermittently there is no fluid communication between either side of the pressure point 62. It is sufficient that an electrical property is substantially changed when the impeller 46 squeezes the internal walls of the pump hose 44 together. The electrical property may for example be resistance, impedance, voltage or current when the pump hose 44 contains an electrically conductive fluid, which aqueous sterilising fluids typically are. Referring to FIG. 6, further rotation of the impeller 46 moves it away from the pressure point 62, and permits the resilient walls of the pump hose 44 to revert to an open configuration wherein fluid at the outlet end is in fluid communication with fluid at the inlet end within the pump hose 44.

By determining (within a specified tolerance level) whether and to what extent a conductive path exists between the electrode clips 52a, 52b, it can be determined whether a conductive sterilising fluid is being cycled through the outlet hose 18 and inlet hose 20, for example via a lumen of an endoscope 16. During normal pumping, a conductive path will exist between the electrodes 52 via sterilising fluid in the outlet hose 18, in the lumen of the endoscope 16, in the sterilising compartment 8, and in the inlet hose 20. In this example, the connector 22 is non-conductive so that when connected to the endoscope, the only conductive path between the inside of the outlet hose 18 and the inlet hose 20 (apart from via the pump hose 44) is via the lumen of the endoscope 16. An electrical property measured between the electrodes 52 will have a substantially constant value. However if this conductive path is interrupted, for example by a blockage in the lumen or by the free end of the inlet hose 20 being above the level of sterilising fluid in the sterilisation compartment 8 so that air is sucked in, the only major conductive path will be via the pump hose 44. In this event, the electrical property that is measured between the conductive fittings 53a,53b will be affected by the internal fluid path within the pump hose 44. If, for example, a voltage is applied to the electrodes 52a,52b, and resistance is the measured electrical property, its value will increase as the impeller 46 squeezes together the internal walls at pressure point 62. If the pressure is such as to provide a complete internal seal, the measured resistance will intermittently rise substantially. If current is measured, its value will intermittently fall substantially. It will be understood that various electrical measurements may be made to determine whether the only major conductive path is via the fluid within the pump hose 44. In a preferred embodiment, the circuit used for the sensing is an oscillator function as opposed to a direct DC resistance function to avoid electrolysis occurring at the conductive fittings 53. If a DC resistance is used then over time one of the stainless steel fittings 53 is liable to tarnish and may build up an insulating oxide layer.

If the measured electrical property is determined to be fluctuating beyond a specified range or limit, the apparatus may be programmed to signal an error condition. Various operating modes and error situations are summarised below.

Normal Operation

As the rotor rotates and when connected to the sterilisation compartment filled with sterilant solution, the conductivity across the two conductive fittings 53 alternates between two states. A short flow (low resistance) within the pump hose 44 and a long path (high resistance) out through the connection via the lumen of the endoscope 16 and through the solution within the sterilisation compartment 8. The frequency of this state change allows determination of the pump speed as the controller 4 knows the state will change twice in each full rotation. In addition, loss of conductivity through either the long path or the short path tells the controller 4 where solution is present in the system.

No Solution

If no solution is present, either because the pump (due to a blocked inlet hose 20) or within the sterilisation compartment 8 (because it has not be adequately filled) one of the states will register an open circuit.

Disconnected Instrument

At the start of the cycle, the pump operates, the initial state is with air throughout the tube set, endoscope and pump hose, so there is no conductivity within a full rotation. As the pump primes solution enters the tube set and the pump enters a state where there is no conductivity when the rotor is not in the mid-point position (FIG. 6). The number of rotations is now counted until there is conductivity across the sterilisation compartment at which point the controller has determined that solution has reached the conductive lumen connector on the endoscope. At this point the controller reverses the pump and counts the rotations back until the conductivity across the sterilisation compartment is lost. This should happen immediately as the lumen at this point is full of air which will be drawn into the tube set. If conductivity is not lost then the controller has determined that solution is being drawn in from the lumen connector and therefore it must be disconnected from the endoscope.

Blocked Instrument

In the event of a blocked instrument (endoscope) there are two methods that the controller can use to detect failure. In the case of a full blockage the pump will not be able to release the trapped air within the tube set. Solution will never reach the lumen connector and therefore the controller will never measure conductivity across the sterilisation compartment.

In the event of a partial block it is possible that enough air will be pushed past the blockage and the pump will be able to pump solution up to the lumen connector. However, once solution reaches the blockage the loads on the pump will increase significantly as the pump tries to counter the pressure build-up in the tube set. Once a cut-off pressure is reached (for example 172 kPa) the current load on the pump motor will have increased to a pre-set threshold within the controller. The controller can then determine that the pump pressure is beyond the limits set by endoscope manufacturers and abort the cycle.

Pump Failure

In the event of a pump failure the conductivity measured between the two conductive unions will remain constant. At the start of a cycle, if the pump fails to operate, the controller will see no conductivity because the tube set is full of air. If the pump fails mid-cycle the controller will see either conductivity across the solution in the pump tube or the conductivity across the solution in the sterilisation compartment but they will not be alternating. This remains true of either electrical or mechanical failure of the pump.

Excessive Wear in the Pump Components

Peristaltic pumps have a finite pump hose life. The materials used over time lose their ability to return to shape after the rotor has passed. This reduces pump efficiency as the volume of solution pumped in each pump rotation drops. In extreme cases the pump hose can fracture or split, resulting in total pump failure. The controller has a number of methods to determine and predict these failures.

Enforced Pump Hose Lifetime

In the present example the pump has a maximum pump hose lifetime of about 100 hours (approximately 3000 cycles as the pump only operates for approximately two minutes per cycle). At this point a warning will be shown to the operator at the start of each cycle. For the next 10 cycles it is possible to clear the warning and continue with the cycle. However, at the $11^{th}$ operation, further cycles will not be possible until the pump hose is replaced and a specific alarm reset procedure documented with the replacement parts is performed.

Pump Hose Wear Detection

The controller can determine wear in the pump hose through a combination of events. As the pump hose wears, the pump efficiency diminishes. At the start of a cycle, when the pump is purging air to draw in solution, the duration of pump operation before conductivity between the two conductive fittings will increase.

As the material memory of the pump tube diminishes the tube tends to flatten and remain at its compressed shape even when not in contact with the ends of the pump rotor. The effort required by the motor to rotate the rotor drops, resulting in a current load drop on the motor controller.

By monitoring these variables and counting pump error states it is possible to predict pump hose failure even in the event that it happens before the preset hose operation lifetime is exceeded.

Pump Hose Failure Detection

If the pump hose fails completely (rupture or split) then the controller will see one of two possible error scenarios. If the tube fails near or at the inlet union then air rather than liquid will be drawn into the pump; then at the start of the cycle the controller will not register any conductivity across the conductive fittings; this will generate a no solution error. The documented troubleshooting steps for this error will include a check of the pump hose for damage.

If the pump hose fails at any point beyond the inlet union then the pump will be able to draw liquid but it will end up pumping this into a sump created within the bottom of the pump body rather than to the outlet connection. This sump will create a path of conductivity across the pump unions which will lack the pump frequency as seen in normal pump operation. The controller can determine that the pump rotor is still rotating by monitoring the current load. This event will trigger a pump failure mode.

Failure to Drain

At the end of a sterilisation cycle the pump resumes operation to purge the instrument's lumen of solution. By monitoring conductivity across the pump unions the controller can monitor the air being pumped into the pump hose. If the sterilisation compartment is empty then the long path of conductivity in the pump cycle will already be open.

As the pump draws air from the sterilisation compartment pickup the pump hose will become empty and the controller will have lost conductivity through both the long and short paths of the pump cycle.

By monitoring current load to ensure the pump is still operating, the controller can operate for a pre-set time threshold to confirm that air has been pumped through the lumen channel and therefore that the endoscope has been purged of solution. The collective result of these detectable events is that the controller can provide full cycle validation within the system. Conductivity of the solution is always assumed, even in the case of high purity water, The steriliant, for example Fuse for Instruments adds ionic compounds which result in a high level of conductivity regardless of water supply, as will be discussed in more detail later. Fuse is a trade mark of Tristel PLC.

In one embodiment, the lid 24 is provided with a magnet 34, and a Hall effect sensor (not shown) is provided on the PCB 70. When the lid 24 is lifted or removed for maintenance of the pump tube or for other reasons, the Hall effect sensor cannot detect the magnet 34 and will not allow the pump head to rotate, providing a kill switch function.

Figure 7:
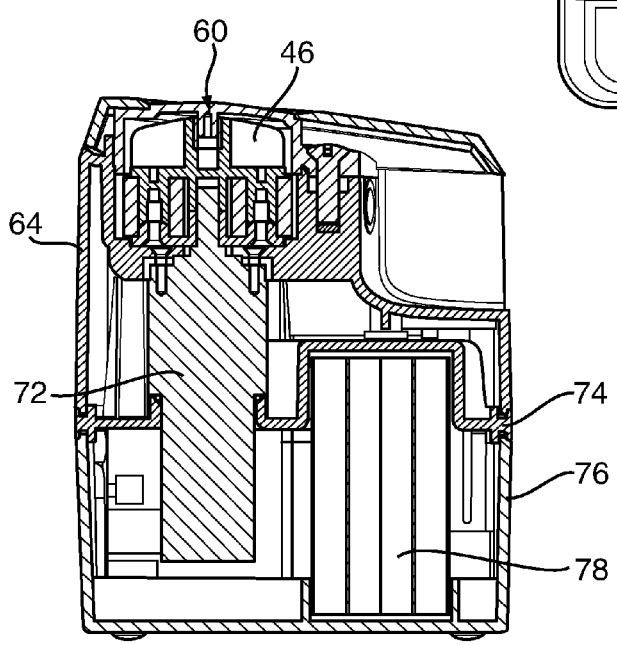
FIG. 7 is a sectional view of the pump of FIG. 5 along the line A-A.
Figure 8:
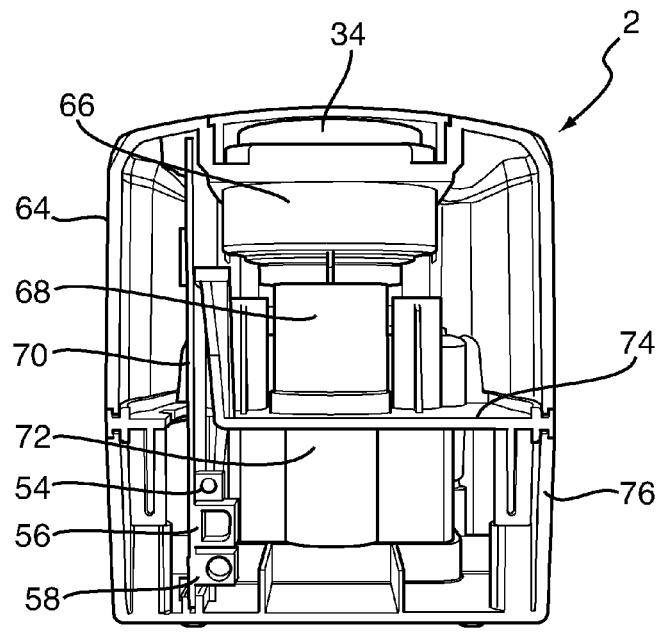
FIG. 8 is an inside rear view of the pump of FIG. 1.
Figure 10:
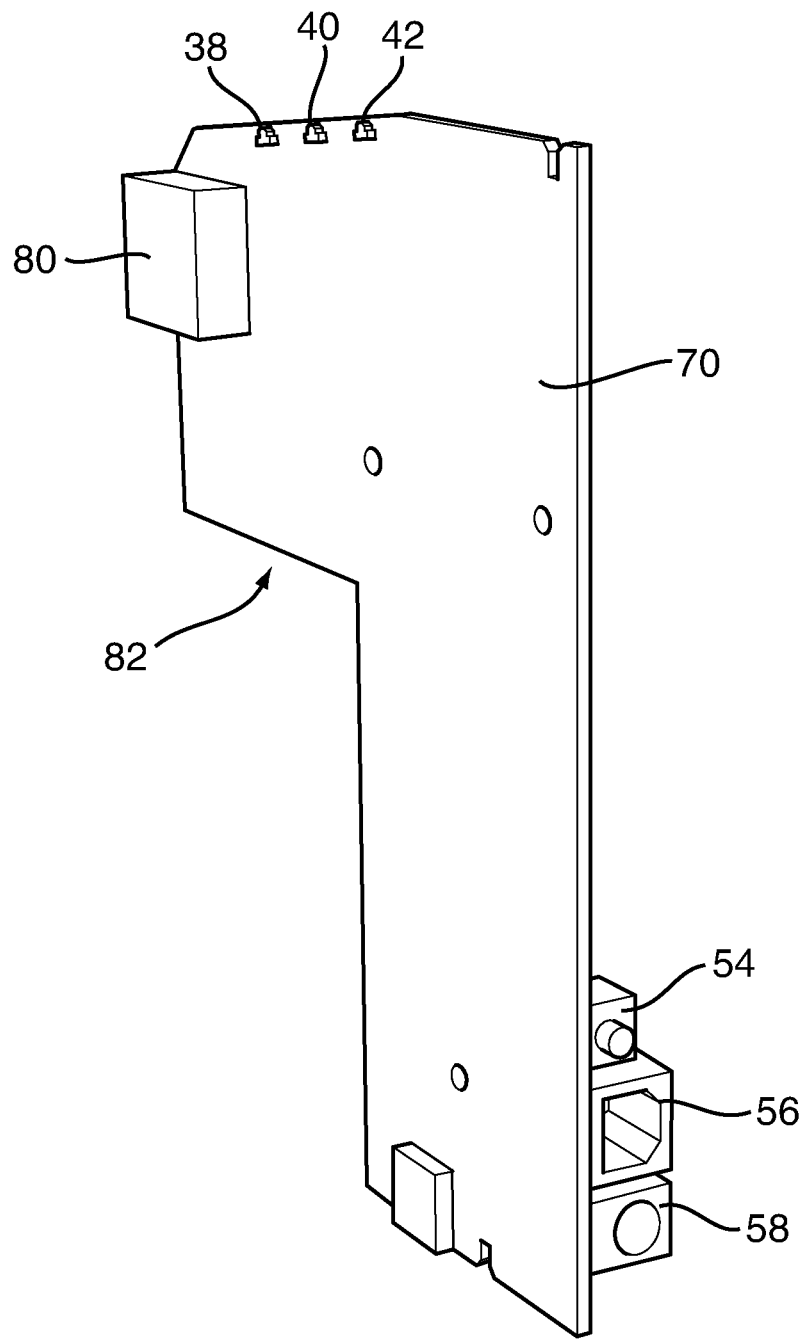
FIG. 10 is a view of the pcb of FIG. 8.

Referring now to FIGS. 7, 8 and 10, internal details of the embodiment of the pump 2 are illustrated. The pump 2 has a chassis 74 on which is mounted a cap member 64 and a base member 76 housing a battery pack 78. A motor 72 drives the impeller rotor 46 within a pump chamber 66 via a gearhead 68. A PCB 70 includes circuitry for applying a voltage to the electrodes 52 and measuring an electrical property. The PCB 70 has mounted on it the reset switch 54, USB socket 56 and power jack socket 58. The rechargeable battery pack 78 is located in a recessed portion 82 of the PCB. A Bluetooth module 80 enables automatic communication with the controller 4.

Example Operation

When the controller and pump are used together using a Bluetooth communication link, with the controller operating as the master unit, once communication is established the system is ready to commence a disinfection cycle as commanded from the controller.

There will be various operation processes depending on the type of disinfectant used, which will require different firmware. Disinfectant is first pumped through the endoscopic device using the pump for a given period of time, for example 1 minute. At the completion of the cycle water (optionally sterile water) and air will be used to flush out any disinfectant residue.

The power status LED 38 adjacent to the power button will indicate the following:

Power ON Green—constant
Battery Low Green—off intermittently

Charge Battery Yellow/Orange—flashing on and off

Battery on charge Yellow/Orange—momentarily flashing Green

Battery Full on charge Green—constant

Product shutdown OFF

The Bluetooth Status LED 40 will indicate the status of the Bluetooth communication link:

Bluetooth search mode Blue—flashing (Waiting for controller to link to pump)

Bluetooth link established Blue—Constant (controller communication with pump)

No Bluetooth activity OFF—No communication link

The pump Status LED 42 will indicate the pump operation and pending automatic control:

pump operating Green—constant pump ready in standby mode Green—flashing momentarily pump failure Red—flashing System Failure Red—Constant No automatic mode OFF Bluetooth Pairing A Bluetooth communication pairing mechanism for the controller and pump will operate. This is achieved by first switching on the pump 2 and then switching on the controller 4 and pressing the 'ON' button again, holding it for 3 seconds to initiate the pairing process. Should the pump 2 need servicing then an alternative pump may be paired with the controller.

Selecting Controller Operating Mode

Press the controller 'On' button twice to activate the select menu;

Option 1—controller (Standalone operating mode)

Option 2—controller+pump (Paired operation with controller and pump)

Option 3—Bluetooth Download (Download controller Event file to PC using Bluetooth com's)

Press 'ON' button to scroll down to the desired option 'StellaCONTROLLER+pump'.

Either option 1 and 2 will be saved to memory as the default when the controller is switched on.

To change this default repeat Stage 1.

Wait 3 seconds and the controller will commence into the chosen mode of operation.

Standard Operation

Press the controller 'ON' button once to switch it on.

Press the pump 'Standby' button 36 to switch it on.

The pump Green Power LED 38 will glow.

The controller will display the Stella™ Logo for 1 second.

The Bluetooth icon will appear while the controller 4 searches for the paired pump 2.

The pump blue LED 40 will flash during Bluetooth search mode.

When the Bluetooth com link is established "Read Instructions" icon will appear for 3 seconds.

The pump blue LED 40 will glow constantly.

The controller ball valve will close, preventing drainage of fluid from the sterilisation compartment 8. Allow 1 minute, after the valve has opened from the last cycle, for fluid to drain before proceeding with the next disinfection cycle.

An animated graphic with "ADD CLEANED INSTRUMENT" will appear for 3 seconds.

The pump Motor green LED 42 will start flashing to indicate automatic pump control.

An animated jug pouring graphic with "ADD DISINFECTANT" will appear.

If moisture is detected in the fluid sensor as valve is closed, then "START CYCLE" will also appear to prompt the user to manually activate the disinfection cycle by pressing the ON button once the sterilisation compartment is full.

Disinfection

The operator adds disinfectant (sterilising fluid) into the sterilisation compartment 8.

When the sterilisation compartment has filled with disinfectant the controller Fluid Sensor (not shown) is triggered.

The disinfectant timer starts. A typical timing is 5 minutes, but times may be varied according to the nature of the sterilising fluid and the item of equipment to be sterilised.

A pie graphic appears to count down and "DISINFECTING" on the controller display 30.

The pump 2 operates for 1 minute pumping disinfectant through the endoscope 16.

The pump Motor LED 42 will glow constant green.

The pump monitors disinfectant pumped through the endoscope.

An animated circulating arrow appears on the top right corner of the controller display 30 to indicate that the pump is operating.

When the pump stops the animated arrow remains stationary.

Drain Cycle

The disinfection cycle expires:

The CONTROLLER valve automatically opens to drain the fluid.

After 10 seconds the pump operates, pumping air into the endoscope to expel disinfectant residue.

The pump verifies that air is pumped through the endoscope for 1 minute.

An animated circulating arrow appears on the top right corner of the controller display while the pump is operating.

When the pump stops the animated arrow halts.

After 1 minute the controller sounds a beep every 30 seconds.

The pump stops.

The Motor LED 42 stops glowing.

A text prompt appears "COMPLETE" with a tick graphic alternating with text "CONFIRM REMOVAL OF INSTRUMENT".

The operator presses the "ON" Button to acknowledge removal of the instrument.

If the valve fails to open then the display 30 displays "REMOVE INSTRUMENT" and a constant harsh sound will continue until the controller is shut down.

Shutdown

The operator presses the "OFF" button or the auto shutdown occurs after 15 minutes.

The controller ball valve stays open.

The pump shuts down.

The controller switches off powering down.

Various failure modes may be displayed in the event of failure of the pump or the controller, and various battery charge modes may be displayed.

The load current of the pump motor 72 can be monitored by the pump system to ascertain overload conditions. Such conditions may occur when the pump is in use as a result of a blockage in the hose or in the endoscope. The base load current will be reasonably consistent while air is pumped through the hose initially; whether the hose is clear or blocked the load current is typically the same, with slightly higher peak current.

Figure 9:
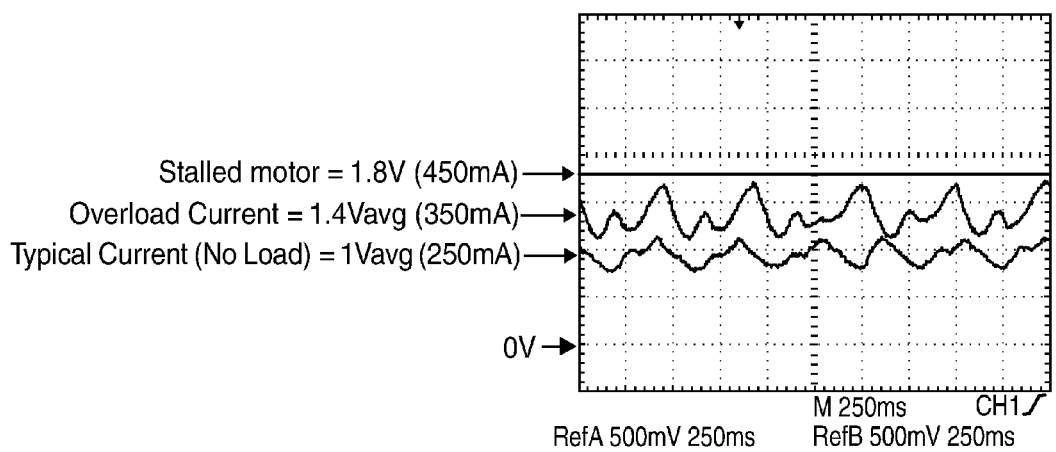
FIG. 9 is a graph of variation in motor load current under different operating conditions.

When disinfectant is present in the hose and there is a blockage present in the outlet hose 18 or endoscope 16 the pump motor current will increase (see FIG. 9). This waveform is measured at the Control Board Micro ADC2 Analogue Input (PF2). The motor typically draws a load current of about 250 mA (1V Avg) when pumping air or sterilising fluid through the endoscope. When a blockage occurs the current increases to approximately 350 mA (1.4V Avg). Under severe conditions the pump will almost stall.

With a stalled pump a Hardware Current Limit will limit the current to 450 mA (1.8V).

Failure Modes:
  A stalled pump motor load current will result in a flat signal level of 1.8V (450 mA)
  In the event of a blocked instrument or hose the motor current signal level will be 1.4V average (350 mA)
  With typical operation while air is being pumped or water is flowing freely the pump motor current signal is 1V on average (250 mA).
  The current load threshold for blockage failure sets the trip after 3 seconds for 300 mA load (1.2V Average).
  The current load threshold for a stalled motor sets the trip level after 2 seconds for 400 mA load (1.6V).

Figure 14:
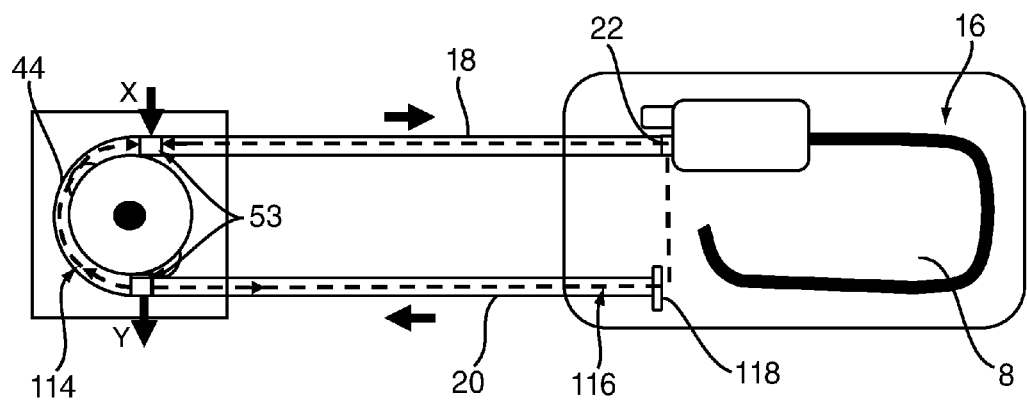
FIG. 14 is a schematic view of apparatus in accordance with another embodiment of the invention.
Figure 15:
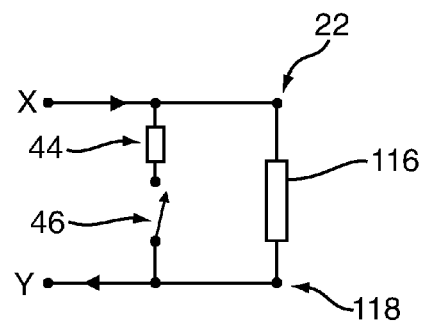
FIG. 15 shows an equivalent electrical circuit for the apparatus of FIG. 14.

Referring now to FIG. 14, an alternative embodiment of the invention uses a conductive Luer-lock connector 22 to connect the free end of the outlet hose 18 to the Luer inlet of the endoscope 16. The inlet hose 20 is provided with an inlet fitting 118 which includes a strainer to remove particulates. The strainer may be made of metal, notably stainless steel. In one embodiment, the strainer includes a metal (preferably stainless steel) weight to ensure that it is submerged correctly. The system can detect that the connector 22 has correctly connected to the Luer fitting on the endoscope 16 or has not unconnected. This is done by pumping liquid, at the beginning of a cycle, through the tube set until it reaches the connector 22. At this point the current 116 is detected via the inlet hose 20 via fitting 118 and the outlet hose connector 22. Once this current 116 is detected, the pump reverses, counting the pump turns that it used to reach the endoscope 16. When the pump turns have been counted the pump should encounter air sucked out of the dry lumen of the endoscope 16. This air can be detected by loss of current, thus determining that the lumen is connected and present. If, at the end of the counted pump turns, the current is still present then liquid has entered the tube set which could only have come from a loose or disconnected Luer lock. This would indicate an UNHOOK and register a fail. An equivalent electrical circuit is illustrated in FIG. 15 for a voltage source X-Y applied via the electrode contact clips 52. An alternative current path 114 through the pump hose 44 is intermittently interrupted by closure of the pump hose by the rotor 46, allowing the current 116 to be distinguished.

Figure 37:
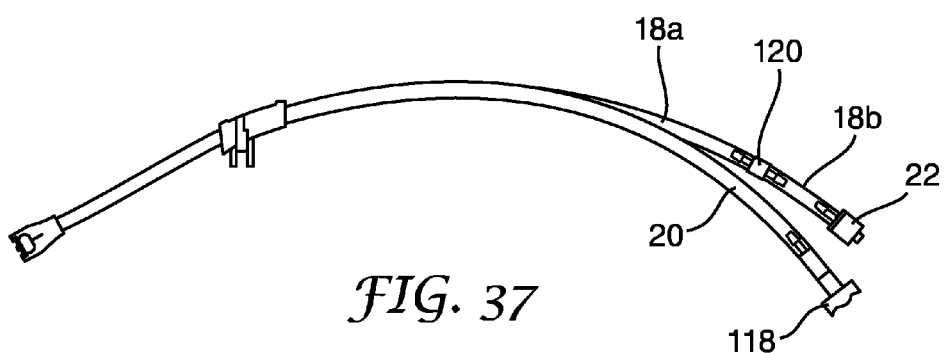
FIG. 37 shows an alternative hose set for use in an embodiment of the invention.

A further embodiment of the hose set is shown in FIG. 37. Here, the outlet hose 18 is in two parts, 18a and 18b, which are connected by a conductive joint 120. This arrangement ensures that the conductive path in the sterilisation compartment is closed slightly prior to the liquid reaching the lumen of the connected endoscope or other instrument. This compensates for inertia-induced overrun of the rotor 46 of the pump 2. In addition it provides a conductive path from the liquid in the tube set to the liquid in the sterilisation compartment in the event that the lumen connection on the instrument is made of a non-conductive material.

Figure 11:
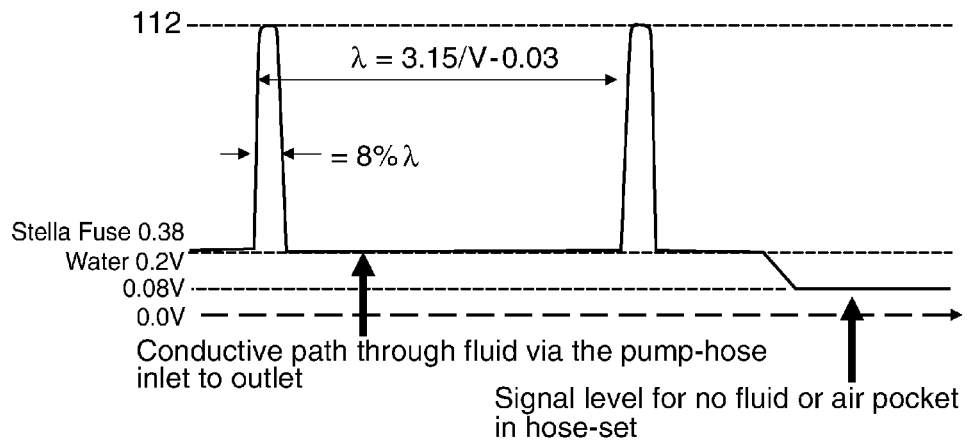
FIGS. 11-13 are graphs showing electrical signals for an embodiment of the invention under different conditions.

An example of the fluid signal is shown in FIG. 11. The peak signal 112 represents the conductive path through the pump hose 44, which is about 8% of the waveform duty cycle. The duty cycle time is estimated $\lambda \approx (3.15/V - 0.03)$ seconds, where V motor is the applied pump motor terminal voltage. The pump rotor speed is estimated $(n \approx 12.5 \times V$ motor) rpm. Different liquids will have different electrical property values. For example, for Stella Fuse™ sterilising fluid, the peak value 112 is about 1V, and the base value for the conductive path 116 is about 0.38 V. Corresponding values for water are respectively 0.6 V and 0.2 V.

The trough portion of this waveform represents the conductive path though the hose-set, starting from the metal outlet hose coupling (X), then through the metal hose coupling 22 on the endoscope 16, through the fluid in the sterilisation compartment 8 then through the intake filter 118 to the metal intake hose coupling (Y). The minimum level (0.08V) is the measured level for no fluid, a circuit design feature that can be used by the system to confirm the fluid sensor circuit is operating.

Figure 13:
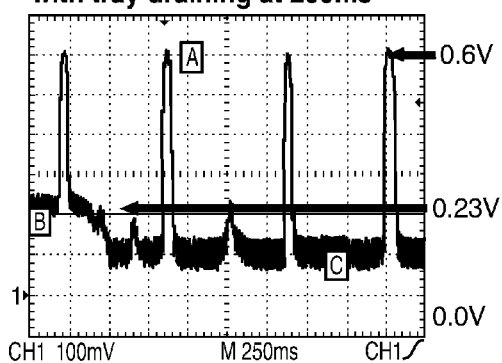

With the pump hose filled with water the peak signal, the current path through the pump-hose, measures ~0.6V (A—FIG. 13) and the trough signal level, the conductive path 116 through the hose-set, measures ~0.2V (B—FIG. 13). With no disinfectant present, while the tray is empty or air pocket is present in the hose-set, the trough signal level is typically 0.08V (C—FIG. 13). For Stella Fuse disinfectant the pump-hose peak measures ~1V and the and hose-set measures ~0.38V. These levels will also depend on mineral content in the water and alternative disinfectant such as Cidex OPA.

Minimum Pump Speed @ 5 Vdc (50-60 rpm)

Figure 12:
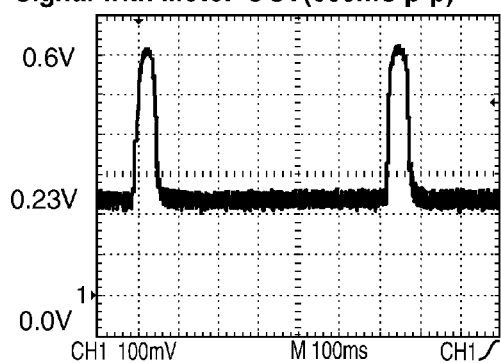

The waveform illustrated in FIG. 12 is at the optimum minimum pump speed (5V) with water pumped through the hose-set. The or each roller 46 opens the pump hose at a duty cycle ~600 ms. With two rollers 46 the peak will appear twice for each pump head revolution, which is ~52-60 rpm @ 5 Vdc. This is the minimum speed requirement to ensure the pump hose 44 will be primed with fluid, at 3 Vdc the pump may not prime should it be elevated more than 100 mm above the intake filter fluid level. This is the result of air back-feeding through the pump hose 44 as it is momentarily opened when monitoring the conductive path 114 through the pump hose.

Prime Pump Speed @ 7 Vdc (80-85 rpm)

To ensure the pump hose 44 is well primed the optimum pump speed needs to operate a margin above minimum pump speed and in this embodiment it is recommended to operate the pump at 7 Vdc (~80-85 rpm).

FIG. 13 illustrates a signal when the sterilising compartment is beginning to drain empty after 200 ms, opening the conductive path 116 through the endoscope coupling and intake filter. The peak signal (A) will continue to appear for approximately 2 to 3 pump revolutions (4 to 5 peaks in the fluid sensor waveform) before air begins to pump though the intake hose and purge out residue from inside the endoscope.

Nominal Pump Speed @ 12 Vdc (140-150 rpm)

The nominal operating speed of the pump is 12 Vdc, which provides a good margin above minimum disinfectant flow rate. For an endoscope of small Luer Channel size, e.g. Ø0.5 mm this speed may reduce to 7-8 Vdc.

Maximum Pump Speed @ 24 Vdc (270-300 rpm)

To purge the endoscope clear of disinfectant the pump momentarily operates at maximum speed to create maximum air drag and remove large residual disinfectant droplets. Once this is achieved the air speed can be reduced, (nominal speed of 12 Vdc) to dry out any further moisture and condensation. In this example, maximum speed is achieved with applied motor voltage 24 Vdc, which is ~270-310 rpm.

Waveform Monitoring

Retained in the system memory are several base line parameters used to help monitor and process the fluid signal waveform. These points include an average value for the peak signal FIG. 13(A), for the fluid path through the pump hose, the average value of the fluid path through the hose-set (B) and the average value for the base level for no fluid present (C).

The conductive properties of disinfectant and water differ therefore two base line parameters are required for both the disinfectant and rinse water for signal levels (A) and (B), as a result five base line parameters are required. These levels will begin as default values in firmware when installed and will slowly integrate towards the average levels over the product lifetime, allowing for slight wear and tear of the pump mechanism and water chemical composition.

These five base line parameters include;
The Peak value when Disinfectant is passing through the pump hose (DP)
 FIG. 16 (A)
The Peak value when Rinse water is passing through the pump hose (RP)
 FIG. 16 (A)
The Average value for Disinfectant passing through the hose-set (DA)
 FIG. 16 (B)
The Average value when Rinse water is passing through the hose-set (RA)
 FIG. 16 (B)
The Average value when No fluid is passing through the hose-set (NA)
 FIG. 16 (C)
Waveform Thresholds To enable the system to monitor when the fluid sensor waveform has reached the required levels various threshold levels are required, which are margins set above and below the base line parameters. These thresholds are fixed into memory but may differ depending on the disinfectant chemistry. The firmware will not be required to adjust the threshold levels. The Peak threshold is used to detect the fluid signal (A) through the pump-hose, the Upper and Lower disinfectant threshold levels used to detect the conductive path (B) through the hose-set and endoscope intake filter (B).

Figure 16:
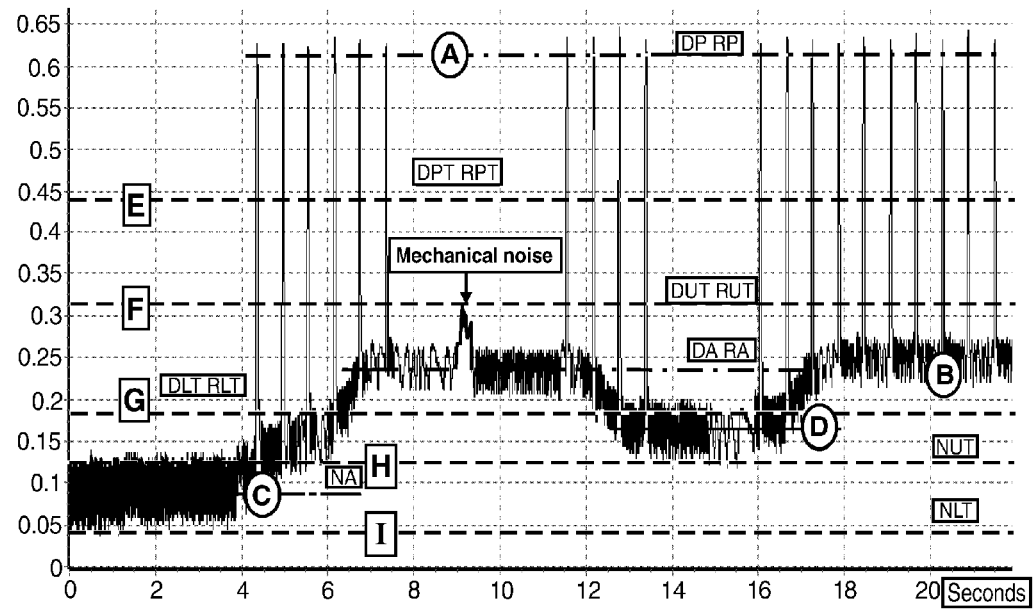
FIGS. 16-33 are graphs showing various aspects in accordance with operation of embodiments of the invention.

Base Line Parameters—FIG. 16
 A Peak signal Fluid conductive path through Pump-hose
 Disinfectant peak trend (DP)
 Rinse water peak trend (RP)
 B Disinfectant/Rinse Fluid conductive path through hose-set
 Disinfectant Average Trend (DA)
 Rinse Water Average Trend (RA)
 C No fluid All of the hose-set or a large portion is vacant of fluid
 'No Fluid' Average Trend) 0.08V (NA)
 D Air pocket in hose A small portion of the hose-set is vacant of fluid
Threshold Parameters—FIG. 16
 E Disinfectant Peak Threshold (DPT)/Rinse water Peak Threshold (RPT)
 F Disinfectant Upper Threshold (DUT)/Rinse water Upper Threshold (RUT)
 G Disinfectant Lower Threshold (DLT)/Rinse water Lower Threshold (RLT)
 H No Fluid Upper Threshold (NUT),
 I No Fluid Lower Threshold (NLT)

The system will track the average trend for fluid conduction over time and update the base line parameters accordingly with sampled averages recorded within these threshold margins.

Four threshold levels are required, which include:
1× Peak threshold FIG. 16—E
1× Upper and 1× Lower threshold for disinfectant in the hose-set F & G
1× Upper and 1× Lower threshold for rinse water hose-set path F & G
1× upper and 1× lower threshold level for No-Fluid H & I
1. The peak threshold (PT) is 70%; Percentage FIG. 16—
 Disinfectant Peak Threshold (DPT)=DP×PT (70%) E
 Rinse Peak Threshold (RPT)=DP×PT (70%) E
2. The hose-set fluid conduction path Upper Threshold (UT) is 150%
 Disinfectant Upper Threshold (DUT)=DA×UT (150%) F
 Rinse Upper Threshold (RUT)=RA×UT (150%) F
3. The hose-set fluid conduction path Lower Threshold (LT) is 80%;
 Disinfectant Lower Threshold (DLT)=DA×LT (80%) G
 Rinse Lower Threshold (RLT)=RA×LT (80%) G This upper tolerance may be higher to allow for mechanical noise caused by roller wear and slight deformation in the pump chamber. See FIGS. 13 and 16 for signal noise.

4. The No fluid Threshold (NT) is Upper threshold is 150% and lower threshold level 50%.
 No fluid Upper Threshold (NUT)=NA×(150%) H
 No fluid Lower Threshold (NLT)=NA×(50%) I This signal is used to determine if the fluid sensor system is functioning. If this signal is not present, the operator will be prompted to check that the relevant port is set LOW to activate the fluid sensor circuit.

During the endoscope detection phase 3 the thresholds DLT and RLT (G) and NUT (H) are used for detecting air sucked back from inside the endoscope.

EXAMPLE

The following parameters would be calculated for the illustrating in FIG. 13 waveform:
Disinfectant peak value DP=1.0V
(A)
Disinfectant Peak Threshold DPT=1.0V×70%=0.7V
(E)
Disinfectant value DA=0.38V (B)
Disinfectant Upper Threshold DUT=0.38V×150%=0.57V
(F)
Disinfectant Lower Threshold DLT=0.38V×80%=0.3V
(G)
Rinse water peak value DP=0.6V
(A)
Disinfectant Peak Threshold DPT=0.6V×70%=0.42V
(G)
Rinse value RA=0.2V
(B)
Rinse Upper Threshold DUT=0.2V×150%=0.3V
(F)
Rinse Lower Threshold DLT=0.2V×80%=0.16V
(G)
No fluid value NA=0.08V
(C)
No fluid Upper Threshold NUT=0.08×150° A=0.12V
(H)
No fluid Lower Threshold NLT=0.08×50%=0.04V
(I)

Production Suite Parameters List

The Production Suite will provide access to the five base line parameters DP, RP, DA, RA, NA, the four tolerance parameters PT, LT, UT and NT and the Motor speed threshold level described in the following section. These parameters may be different for each disinfectant chemistry type firmware variant and may be adjusted as experienced is gained with different chemistries and range of sizes for endoscope Luer channels.

Disinfection and Drain Cycle Process

Figure 17:
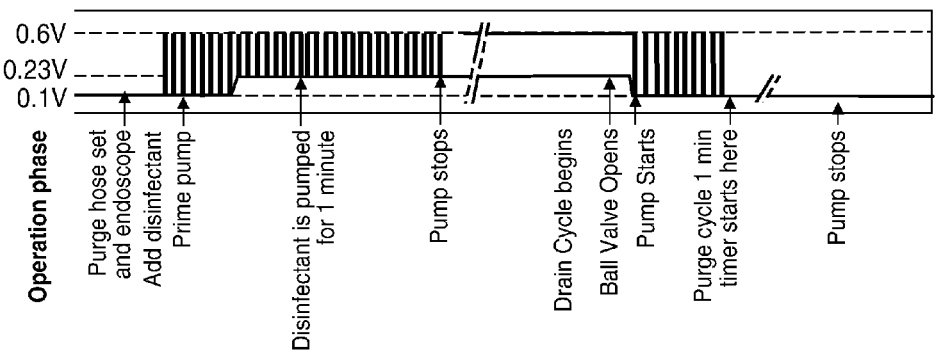

The fluid sensor waveform illustrated in FIG. 17 would be typical during a disinfection cycle and drain cycle process, excluding any rinse cycles.

Disinfection Clean Cycle Phases

The Disinfection clean cycle for the exemplified embodiment is managed in eight phases:

Phase 1 Purge residue from hose-set and endoscope while
Controller displays: Add Disinfectant
When tray is full with disinfectant the controller begins the disinfection cycle
Phase 2 Pump priming—fill the hose-set with disinfectant
Phase 3 Pre-Cycle Endoscope detection
Phase 4 Disinfecting Luer Channel
Phase 5 Pump stops—close pump hose
Drain cycle (Disinfection timer expires)
Phase 6 Post-Cycle Endoscope detection
Phase 7 Purge Endoscope of residue
Dry Endoscope from condensation
Phase 8 Cycle Complete—Confirm Removal of Instrument The Pre-Cycle and Post-Cycle Endoscope detection is confirmation the endoscope is connected during the entire disinfection process and inform the operator should the endoscope fail to be detected.

This process may only be performed at the pre-cycle and post-cycle phases should multiple Rinse cycles take place between. The pre-cycle and post-cycle endoscope detection phases are performed differently, where information from the pump priming phase is used to for the post-cycle endoscope detection phase. Each phase of an exemplary disinfection process is described below.

Phase 1 Preliminary Purge

Both the controller and pump are switched on and establish communications.

During 'Add Instrument and Add Solution' before closing the ball valve the Controller instructs the pump to operate for 6 seconds at 12 Vdc to purge out any residue from inside the hose-set and endoscope that may reside from previous cleaning or failed clean cycle.

Phase 2 Pump Priming

The controller closes the ball valve. Once the tray is filled with disinfectant the controller "Disinfecting" timer begins and instructs the pump unit to begin the prime cycle.

The pump motor operating at 7 Vdc will prime the pump with disinfectant until the fluid sensor peak signal appears (A) with disinfectant in the pump hose.

At this point the pump motor voltage is reduced to 5 Vdc to minimum operating speed, the trough portion of the waveform is ~0.08V (C).

The system counts all of peak signals A (path 114 through the pump-hose) while pumping disinfectant through the outlet hose and stops immediately as the conductive path 116 is complete through the endoscope coupling and intake filter, the trough portion of the waveform (B), (0.38V), which is typically 5-7 peaks (FIG. 16). The number of peaks is temporarily saved to memory for the post-cycle endoscope detection.

Phase 3 Pre-Cycle Endoscope Detection

Now the hose-set is completely filled with disinfectant; however air remains inside the endoscope at this stage. The pump will now momentarily reverse slowly at 5 Vdc just enough and stop when the conductive path through the fluid signal has dropped on average below the Disinfectant Lower Threshold DLT (80% DA). This is the result of air being sucked back into the outlet hose that remained in the endoscope (88), opening the conductive path (D). See FIGS. 16 and 18.

Figure 19:
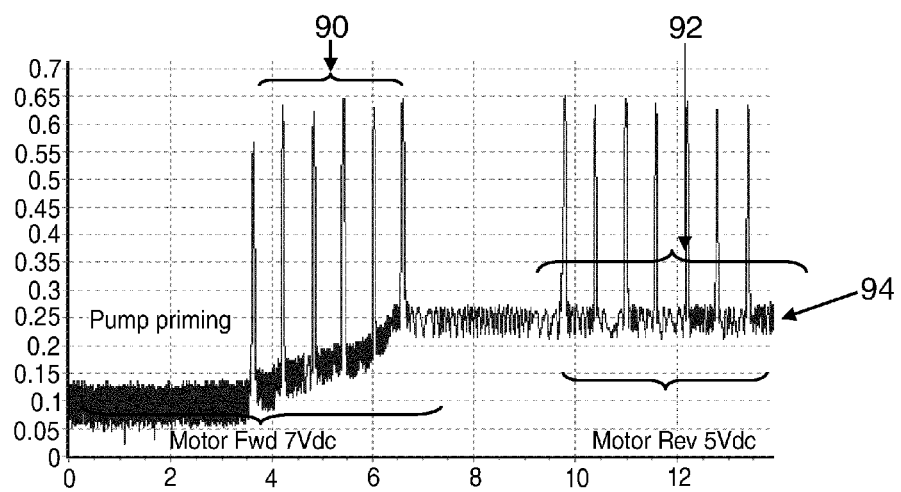

If the endoscope is not connected then disinfectant will be sucked back into the outlet hose instead, therefore the conductive path through the hose-set will remain steady (94), confirming the endoscope is not connected (B) (FIG. 19).

Figure 18:
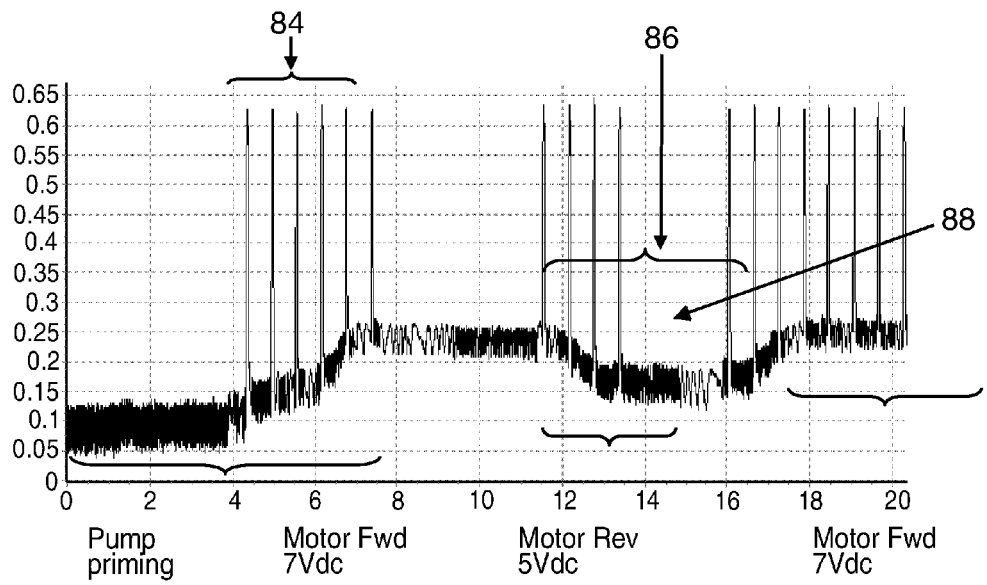

FIG. 18 Endoscope detection confirmed
Phase 1—Outlet hose filled in 5 peaks (84)
Phase 2—Air sucked back opens conductive path (86)
FIG. 19 Endoscope detection failure
Phase 1—Outlet hose filled in 5 peaks (90)
Phase 2—Fluid sucked back maintaining conduction (92)

Report Failure and Purge after Drain

If the endoscope is not connected, the pump will stop and instruct the controller of the failure code, the controller will open the ball valve and display the failure "Instrument Unhooked".

After the 1 minute drain cycle when the tray has drained empty the pump will operate for 10 seconds at 12 Vdc to purge the hose-set from disinfectant.

Pump Motor Overload

Figure 21:
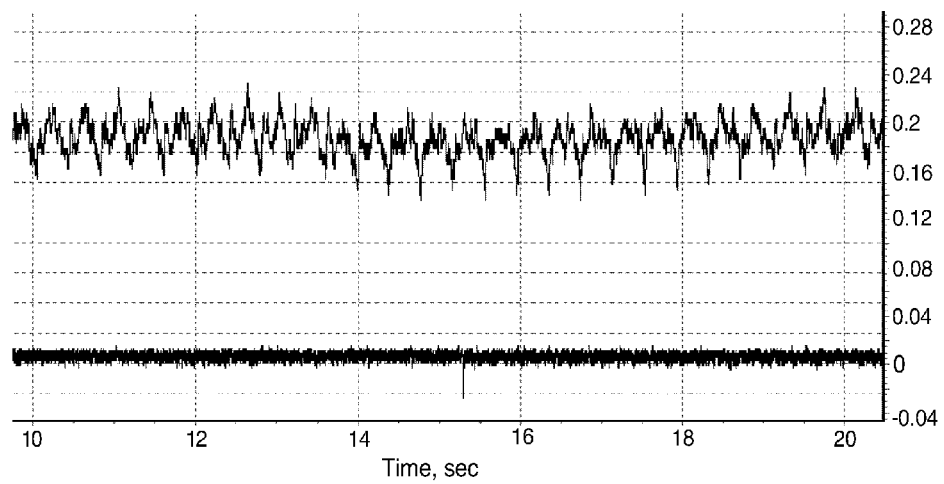

The pump system must protect the pump from current overload and the pump hose from pressure overload. Should the outlet hose or endoscope become blocked at any stage the motor load current will exceed typical load current 230 mA. FIG. 21 illustrates an overload condition.

Pump Failure (Over-Current Trip)

If the pump head is stalled, either from an oversized pump hose being fitted or mechanical interference, the hardware current limit will only deliver 400 mA maximum. The current trip threshold is set to 380 mA, if the average current level is measurement constantly above this threshold for more than 3 seconds then the pump will stop and instruct the controller of pump failure. The controller will open the ball valve, record the Over-current Trip failure and display "Pump Failure".

Blocked Instrument

If there is a blocked hose or endoscope the average load current will reach above 350 mA. If this situation remains for more than 5 seconds the pump will stop and inform the controller of the Failure Code for Blocked Instrument. The controller will open the ball valve, record the failure and display "Blocked Instrument".

Overload Time-Out

Figure 20:
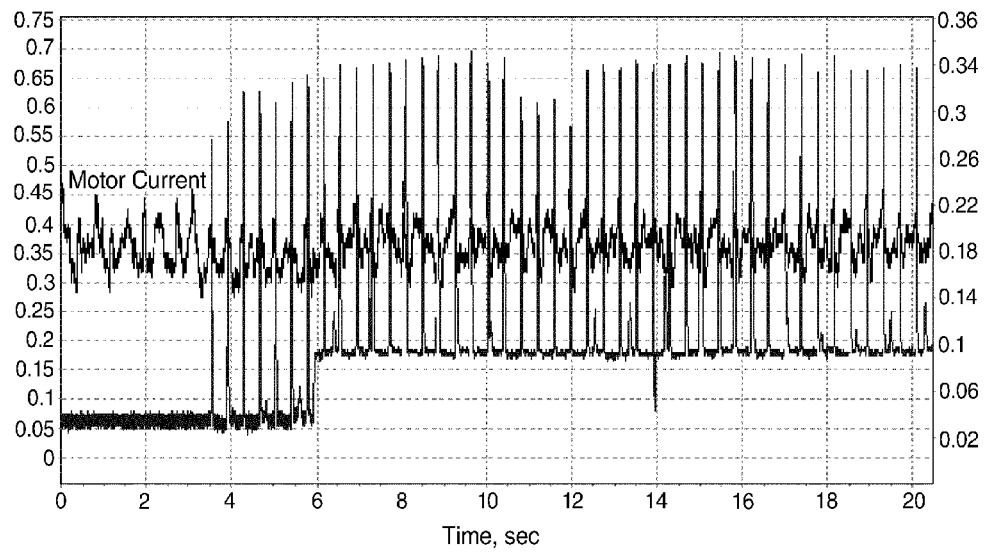

If the average load current reads above 230 mA as a result of a small Endoscope Luer channel, then the system will reduce the applied voltage to decrease the pump speed until the average load current has reduced to 230 mA. If the applied motor voltage has reached 5 Vdc and the average load current remains above 300 mA for more than 5 seconds then the pump unit will stop the rotor and inform the controller of the Pump Overload time-out. The controller opens the ball valve, records the failure code for Overload time-out and display "Blocked Instrument". FIG. 20 illustrates a normal load condition.

The average motor current may still remain above 230 mA but below 300 mA for an endoscope with a small diameter long Luer channel. In this situation the system continues with the disinfection cycle.

Figure 22:
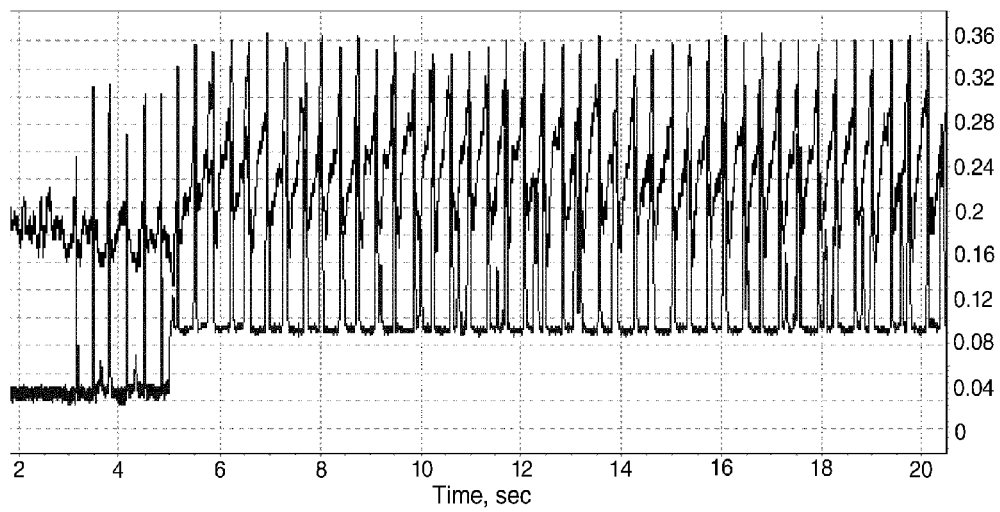

The waveform of FIG. 21 illustrates that for a 0.5 mm Luer channel with applied motor voltage of 12 Vdc the motor load current on average is above 300 mA, 70 mA above the nominal load current 230 mA. In this regard the pump system will reduce the voltage on the motor until the average load current is settled at 230 mA. FIG. 22 shows a waveform where the average load current has been reduced on average to 230 mA with an applied motor voltage of 8 Vdc.

The system needs to register this condition has occurred, so that during Phase 8, the 1 minute Purge cycle, the pump motor voltage will NOT operate the purge at 24 Vdc for 15 seconds, but remain at 12 Vdc for the entire 1 minute purge cycle.

Pump Pressure Overload

If an endoscope with a small diameter long Luer channel is fitted to the Pump unit the trough portion the fluid waveform in FIG. 16 (B) may appear on average above the Upper Threshold (DUT) (2), which will be due to high pressure causing back feed through the pump hose.

If this situation continues for more than 5 seconds the pump speed is reduced by decreasing the motor voltage until the trough portion of the valve is on average below the Upper Threshold.

Motor Current Overload Waveform

Figure 23:
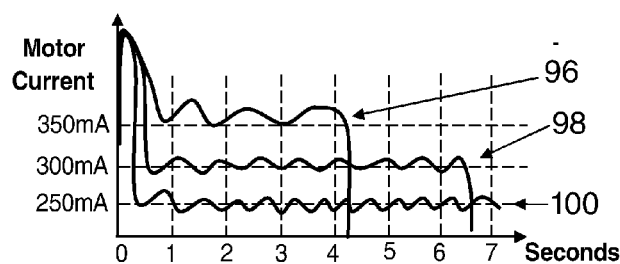
Figure 24:
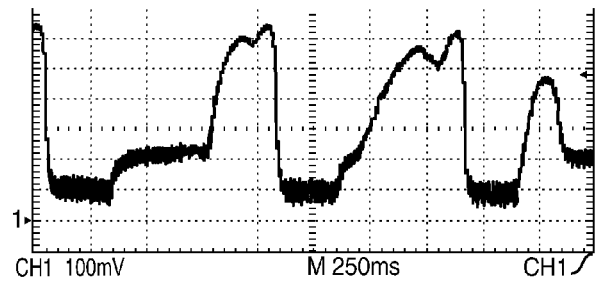

Referring to FIG. 23 a typical load current 100 for normal pump operation is about 250 mA. A waveform 96 of 350 mA for more than 3 seconds causes the unit to stop pumping; or a waveform 98 of 300 mA for more than 5 seconds causes the unit to stop pumping if the motor voltage has reached 5 Vdc. If the motor speed has dropped to the minimum (5V) and the situation still remains after 5 seconds then the pump unit will stop pumping and inform the controller of the Pump Overpressure time-out. Referring to FIG. 24, the controller will open the ball valve, record the failure code and display "Blocked Instrument". In the event of consistent failures a perished pump hose will be replaced.

Luer Channel Disinfection

After it is confirmed the endoscope is connected then proceed to operate the pump in the forward direction at 5 Vdc for 10 seconds then 12 Vdc for 90 seconds to complete the Luer channel disinfection. This initial reduced speed allows the system to respond better to a potential blocked instrument or hose-set.

Phase 5 Disinfection Pump Cycle Stops

Figure 25:
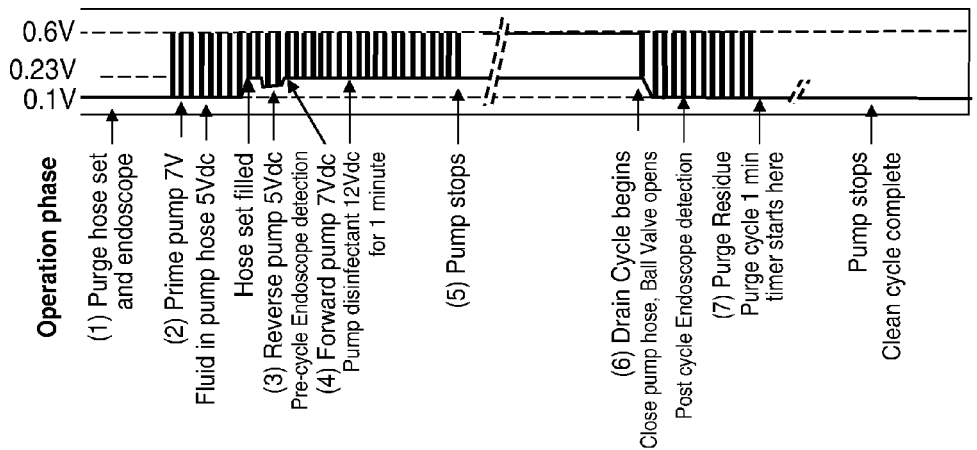
Figure 26:
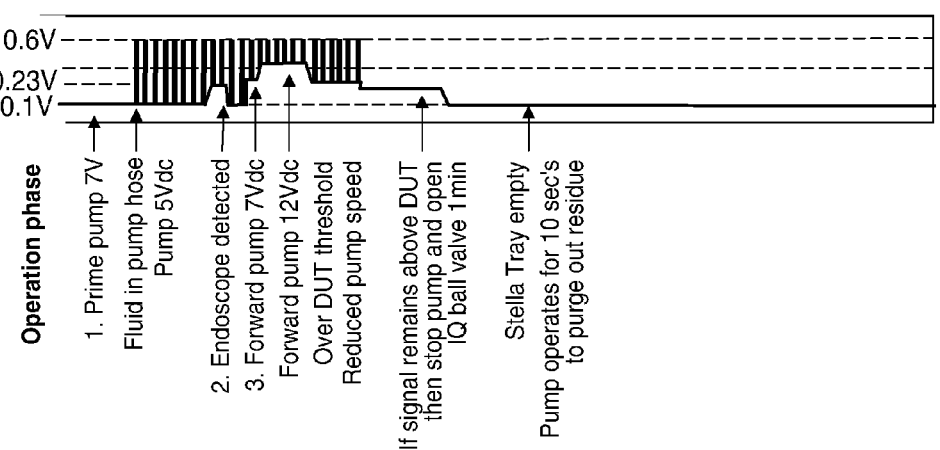

Waveforms for exemplary disinfection cycles are illustrated in FIGS. 25 and 26. After pumping disinfectant through the endoscope Luer channel for 1 minute the pump stops and the disinfection process continues for the remaining 4 minutes.

Closing the Pump Hose 5 seconds before the disinfection timer expires or the last Rinse cycle for a specified disinfectant is completed, the pump unit must ensure the pump hose is closed so that disinfectant or rinse water will not siphoned out during the drain cycle before it has time to confirm the endoscope is connected. During this 5 seconds before opening the ball valve for the drain cycle the controller instructs the pump unit to 'close pump hose'. The pump unit applies 5V to the pump motor for 5 seconds to ensure disinfectant is present in the endoscope and then operates the pump motor in short bursts at 5V until the pump hose has closed. This is confirmed by ensuring the fluid conduction signal through the hose-set is within the disinfectant upper and lower thresholds. See FIG. 16. between threshold level (2) and (3). After this the controller proceeds to the 1 minute drain cycle.

Leak Failure

During this phase if no fluid is detected the pump unit stops the pump and informs the controller of Leak failure mode, the controller opens the ball valve, records the failure and displays failure "Leak".

Phase 6 Drain Cycle

During the Drain Cycle, (After the disinfection cycle or last rinse cycle) the controller instructs the pump unit to perform a Post-Cycle Endoscope detection and purge cycle to expel the residue from inside the endoscope. The post endoscope detection confirms it has not become disconnected during the disinfection cycle or rinse cycles.

Post-Cycle Endoscope Detection

The controller opens the ball valve to commence the drain cycle and 30 seconds later instructs the pump unit to confirm the endoscope is connected. The pump unit applies 5V to the pump motor and stops immediately when the conductive path through the hose-set is no longer detected, FIG. 16 Peak signal (A). At this stage disinfectant still remains in the outlet hose and the endoscope Luer channel. The pump motor will now reverse at 5 Vdc while at the same time using the fluid sensor to count the number of peaks that appear when the disinfectant from the outlet hose and endoscope is pumped back into the inlet hose. The pump will then stop immediately as soon as the fluid sensor no longer detects disinfectant in the pump hose.

The number of peaks represent the combined length of the outlet hose and endoscope. This number has subtracted the previous value stored to memory at Phase 2 Pump priming. If the result is greater than 0 then the endoscope is found to be connected. If the remainder is less than 0 or equal this would indicate the endoscope is no longer connected to the hose-set, becoming disconnected during the disinfection process. The difference will vary depending on the inside diameter and length of the Luer channel.

Valve Failed to Open

If during the reverse operation fluid is constantly detected for more than 1 minute the pump unit stops the pump and informs the controller of failure "Valve failed to open. The controller will again attempt to open the valve for 3 seconds, record the failure and displays the failure: "Valve Failed to Open" and "Remove Instrument".

Figure 27:
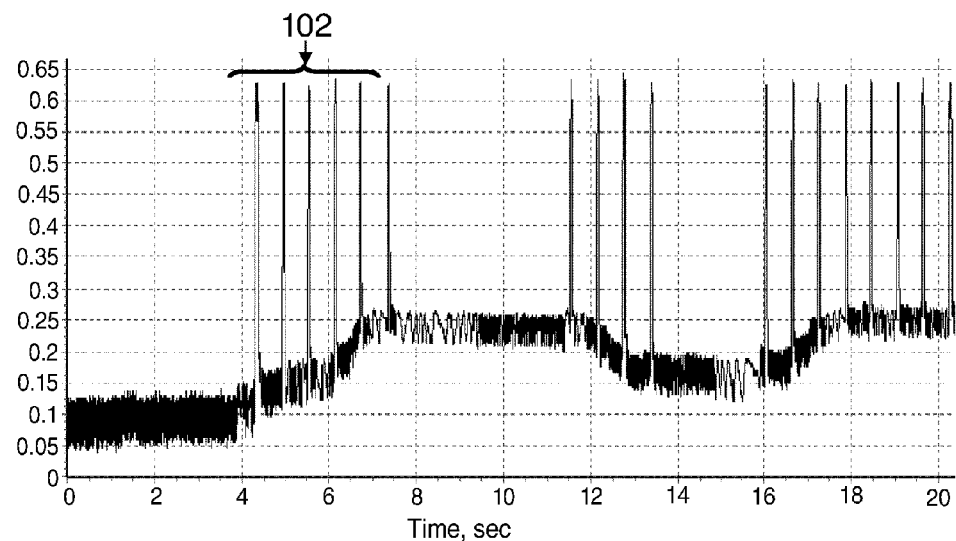

FIG. 27 Pre—Cycle Endoscope detection

In the illustrated waveform, 5-6 Peaks 102 are required to fill the outlet hose.

Figure 28:
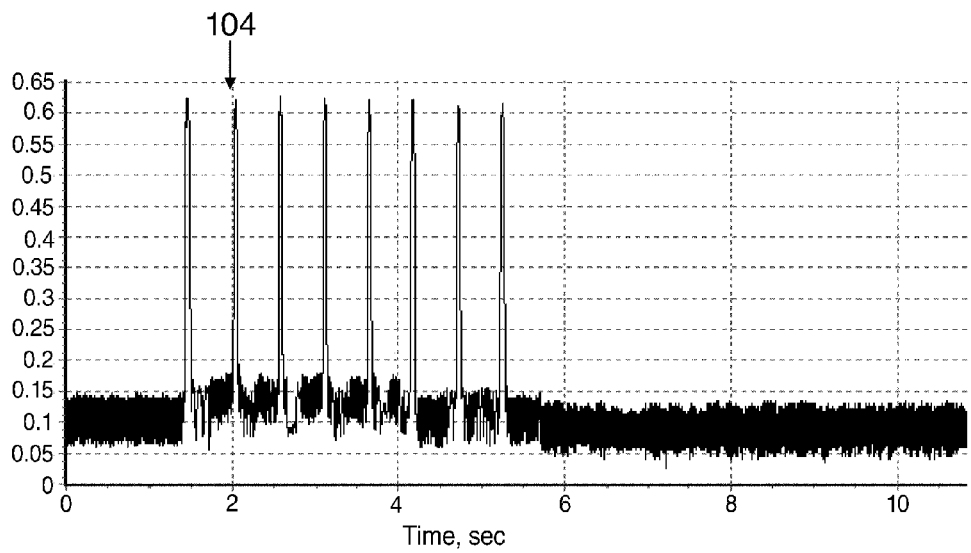

FIG. 28 Post-Cycle Endoscope Detection.

In this waveform, 8-9 Peaks 104 are required to empty the outlet hose as fluid is sucked back from the outlet hose and endoscope.

Figure 29:
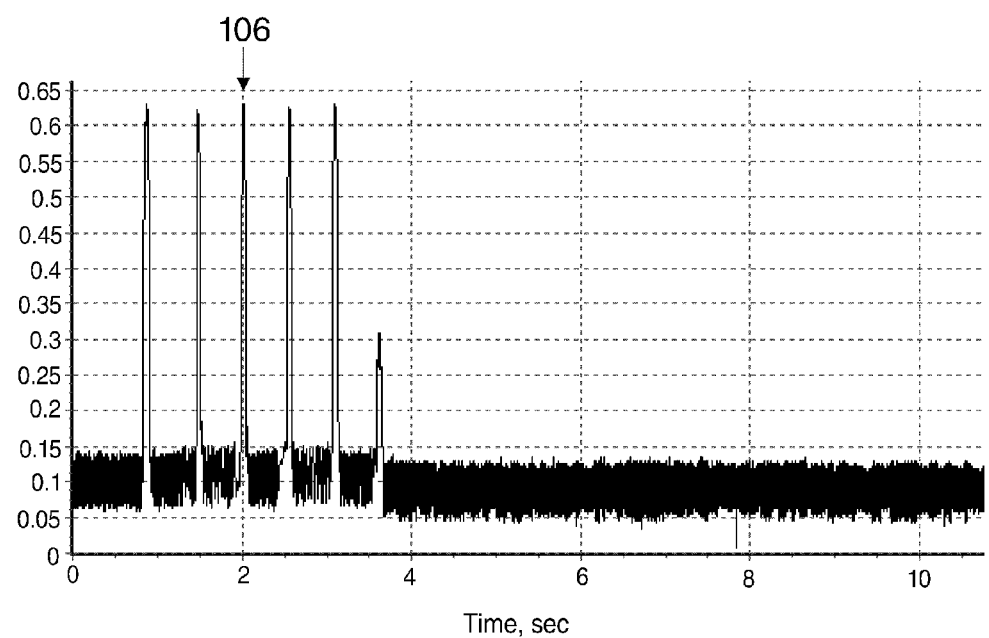

FIG. 29 Post-Cycle Endoscope Detection Failure.

Only 5-6 Peaks 106 are required to empty the outlet hose as fluid is sucked back from the outlet hose and endoscope. This waveform illustrates that the endoscope has failed to be detected as only 4 to 5 peak fluid signals appear, less or equal to those counted in FIG. 28.

Report Failure and Purge after Drain

If the endoscope is not connected the pump will stop and instruct the controller of the failure, the controller will check the ball valve is opened, record the failure and display the failure "Instrument Unhooked".

After the 1 minute drain cycle the pump is operated at 12 Vdc to purge the hose-set from disinfectant.

Phase 7 Purge Residue

Purging Residue and Drying Endoscope

The pump continues in the forward direction at 5 Vdc for 5 seconds to purge out any disinfectant or rinse water residue in the hose set and endoscope. After the 5 seconds the pump speed is increased, if the pump speed during the disinfection was not able to operate at 12 Vdc (Overload Time-out) then apply 12 Vdc to the pump motor for the remaining 1 minute purge cycle.

If the pump was able to operate at 12 Vdc during the disinfection cycle then apply 24V for 15 seconds, purging out any large residual particles in the hose-set and endoscope.

The speed is then decreased with 12 Vdc applied to the motor for the remaining 40 seconds, pumping air to dry out the Luer channel from condensation.

Purge Mode Failure

During the purge mode if fluid is continually detected for more than 1 minute this would indicate that the controller ball valve has failed to open.

Phase 8 Cycle Complete—Confirm Removal of Instrument

When the Disinfection cycle, Rinse cycle and Post-Endoscope Detection is confirmed and the final Purge cycle is complete the pump unit informs the controller of a successfully clean cycle. The controller will now issue a Validation code to the operator, recording the time and validation code as per the standard controller operating procedure.

Perished Pump Hose and Replacement
Consecutive Overload Failures

If the pump unit has stopped the disinfection cycle 5 times consecutively for Motor Over-current Trip, Pump Overload Timeout or Over-pressure timeout, this may indicate the pump hose has perished, the wrong pump hose is fitted or some form of mechanical interference.

With continuous wear the pump hose will fail and possibly rupture causing fluid to leak into the pump chamber creating an electrical conductive path directly between both hose couplings.

Should this occur the fluid signal level will appear constantly above the Peak Threshold (1) while the pump is operating or not. In these circumstances proceed to failure "Replace pump hose".

Perished Hose Detection

Should the operator choose to reset the "Replace Pump Hose" alarm without taking action to replace the pump hose, this will eventually lead to a hazardous situation for the patient. The hose will become flat to the point where the pump will no longer deliver the required disinfectant flow rate, exposing risk of cross contamination from one patient to the next. As there is no other means for monitoring the disinfectant flow rate this situation must be well monitored and stop further disinfection cycles and again alert the operator to replace the pump hose.

A severely flattened pump hose will have less fluid present inside, the result is the peak signal in the fluid sensor waveform will diminish below the original level of 1V for disinfectant and 0.6V for rinse water. See FIG. 16 (A).

This information will enable the pump system to process the state of the pump hose and take action to stop further disinfection cycles accordingly.

To manage this situation the fluid sensor waveform peak signal level is compared with the original level when the hose was new. Separate Original Peak values for Disinfectant and Rinse water (DPO) and (RPO) are recorded into memory when the pump hose is new or has been replaced. This Original Peak valve (DPO) (RPO) will be updated by a small percentage each time the hose is replaced after 100 hours of pump operating time. The original peak values will integrate rapidly in the positive direction and very slowly in the negative direction, allowing for the aging hose effects and should the operator not replace the hose before resetting the "Replace Pump Hose" alarm.

Method for Updating Original Peak Values

After the pump hose has just been replaced or the first time for the pump to operate, (e.g. the operator has reset the "Replace Pump Hose" alarm), the system will record during the next consecutive disinfection cycle and rinse cycle the average peak signal levels above the peak Threshold (1) (DPT) and (RPT) using the original peak value trends (DPO) and (RPO). The difference between the average and peak levels (DP) and (RP) and the Original peak values (DPO) and (RPO) are calculated at the end of the disinfection clean cycle. The integrator will then update into memory with the Original peak values (DPO) and (RPO) by +20% I-5% of the difference calculated. The integrator is designed to responding quickly to a positive differential than a negative differential to compensate for an operator consistently resetting the "Replace Pump Hose" alarm but does not actively replaced the pump hose.

Pump Hose Expiry

The pump unit is to count the number of minutes of pump operation. After 100 hours (6000 minutes) the pump unit informs the controller that the pump hose has expired. The controller will display the warning "Replace Pump Hose" for 5 seconds once communications has established with the controller and after each time the operator has pressed the controller 'ON' button to "Restart Cycle". The operator will be able to continue 10 disinfection cycles before the controller will no longer permit further disinfection cycles to begin, at which time the pump hose must be replaced. This process allows the operator time to continue with further disinfection cycles throughout the day and replace the pump hose at the end of the day.

If the hose has not been replaced by this stage the pump unit will inform the controller that no further disinfection cycles can take place, the controller will constantly display "Replace Pump Hose" and will not proceed further beyond this warning and auto shut down as normal.

Replacement of Pump Hose

At this stage the pump LED will flash red.

When the pump hose has been replaced the operator will need to plug in the PC USB cable or Power Adaptor into the pump unit and press the pump Standby button for three seconds to acknowledge the pump hose has been replaced, at which time the pump Red LED will stop flashing.

Pump Speed

The Pump head rotates at about 1 revolution per second at 5 Vdc.

The motor will stop within 100 ms (36°) when operating at 5 Vdc.

Protection of Motor Reverse Relay

When changing the direction of pump, first set the motor voltage to 0V for 300 ms before changing the relay state, then apply the motor voltage for the pump to operate in the opposite direction. This allows enough time for the motor to come to a complete standstill and avoid current flow and electrical arcing while changing over the motor relay contacts, thereby providing optimum lifetime of the Motor relay.

Pump Speed Information

FIG. 30 Pump Rotor Speed versus Applied Motor Voltage

Figure 30A:
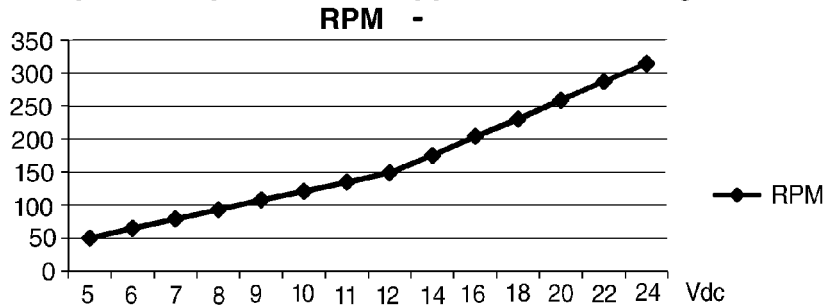
Figure 30B:
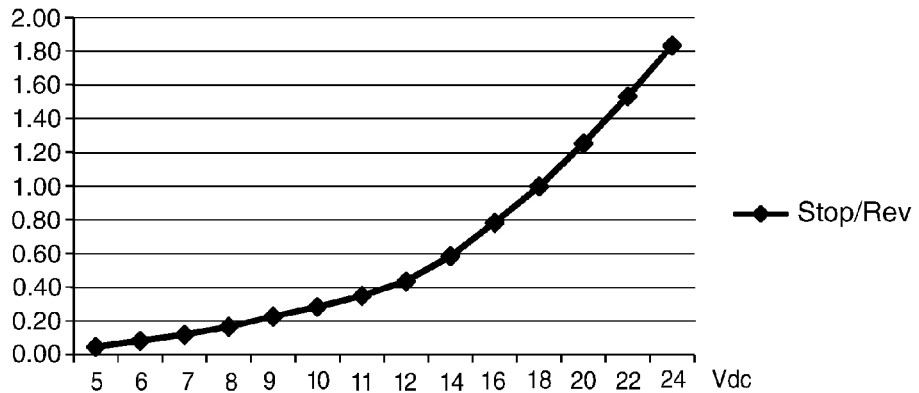
Figure 30C:
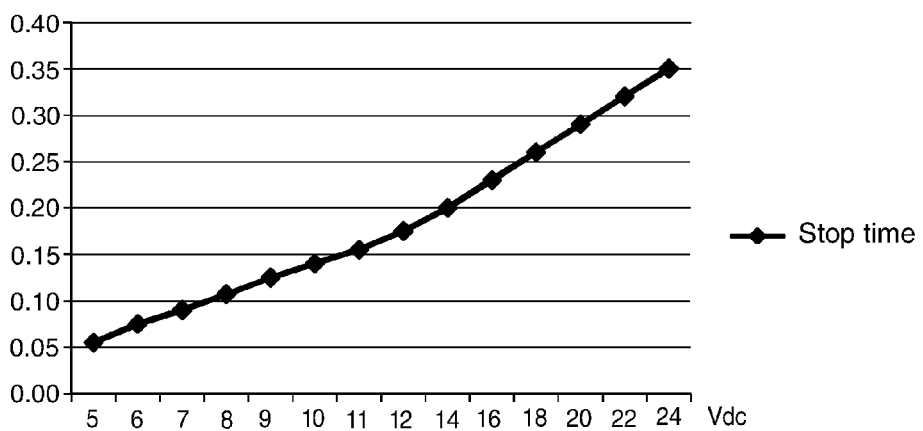

FIGS. 30a-c illustrate the pump head rotation speed (a), the number of revolutions (b) and the time (c) before the pump is standstill after power has been removed, which is the minimum time required before changing the reverse relay contacts over and reapplying power to the pump motor.

This detail is recorded with the pump hose fitted while pumping air, which is the maximum expected speed and time before standstill. These levels will reduce under load conditions when pumping disinfectant and smaller Endoscope Luer channel diameter size.

Figure 31:
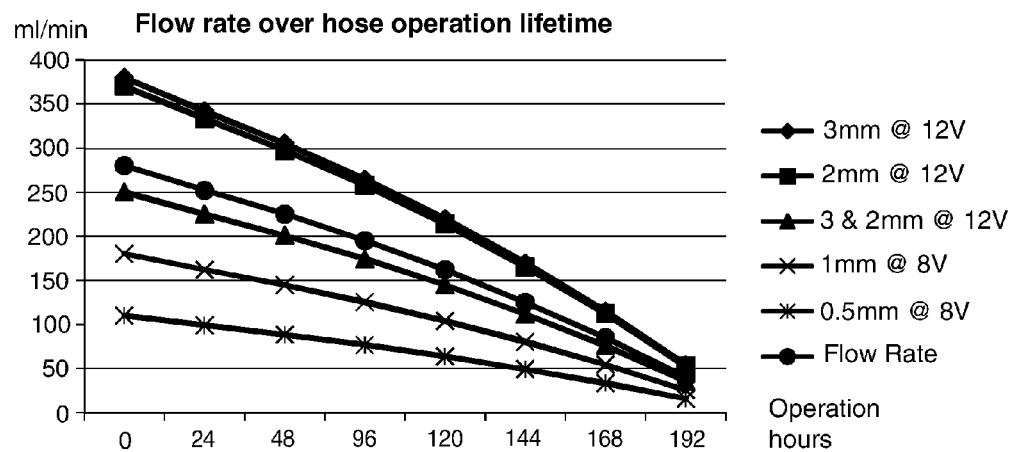

FIG. 31 graphs Flow rate over pump hose operation lifetime for an endoscope with a Luer Channel of 0.5 mm diameter and a pump motor voltage at 8 Vdc. This is the optimum operating voltage for this size of endoscope Luer channel. Increasing the speed does not improve fluid flow rate due to back pressure created by the size of the small Luer channel diameter. This information is based on a model of an Endoscope that is 0.5 m long and has a 0.5 mm diameter Luer Channel. With the hose operation lifetime limit of 100 hours the hose is sufficient for a 1 mm diameter Luer channel.

For some endoscopes it is desirable to limit the pressure, for example to a maximum of 20-24 PSI (138-165 kPa). Many endoscope manufacturers specify a maximum allowable pressure of 25 PSI (172 kPa). We propose to limit the voltage to the motor which should stall the pump at the desired pressure. Alternatively a spring-loaded pump head roller (rotor) may be used, which releases pressure in the pump hose at a desired pressure level.

Fluid Sensor Tests and Threshold Levels

The performance of fluid detection system must be consistent and reliable to ensure this automated process runs smoothly without adverse interruptions throughout the lifetime of the product. It is desirable:

1. To identify if there is a clear difference in the fluid signal levels for tap water, both soft and hard water with a higher mineral content, and the disinfectant.

2. That the signal for the disinfectant remains consistent over a period of 170 hours of exposure time and with 50 hours of pump operating time.

Figure 32:
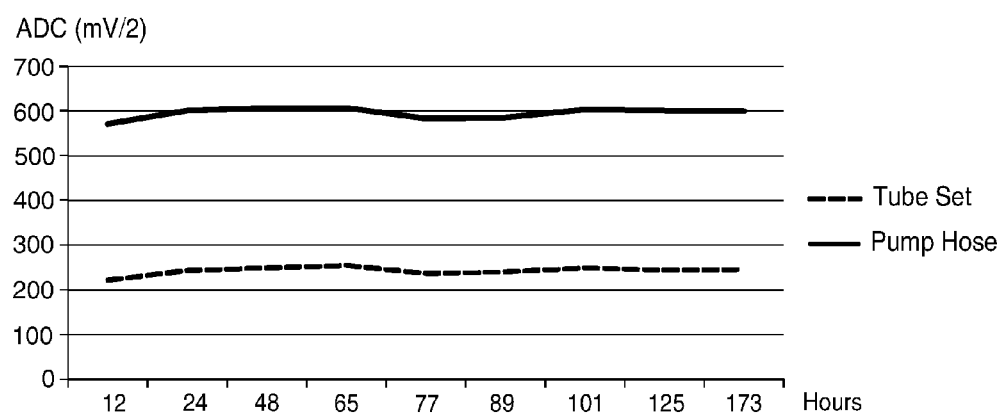

FIG. 32 shows the fluid sensor signal trend as measured over 170 hours and 50 hours pump operation for an embodiment of the invention. The analogue reading is measured by the micro; for the equivalent voltage reading multiply by 2.

Over 170 hours of exposure time using nine disinfectant batches the fluid sensor signal level in the pump hose varied from 1140 mV (570 on the graph) to 1210 mV (605) with an average 1188 mV (594+2%, −4%). The tube set signal level varied from 442 mV (221) to 508 mV (254) with an average 484 mV (242+5%, −8.5%). The dips in the signal level were attributed to aging disinfectant solution, observed about 80 hours in FIG. 32, or the level of mineral content in the water. The conclusion from these test results is that the fluid sensor signal levels will remain reasonably consistent for over a period of 170 to 200 hours and the pump hose for 50 to 100 hours of pump operating time. Any inconsistency after this time may indicate it is time for the operator to replace the pump hose and tube set.

Figure 33:
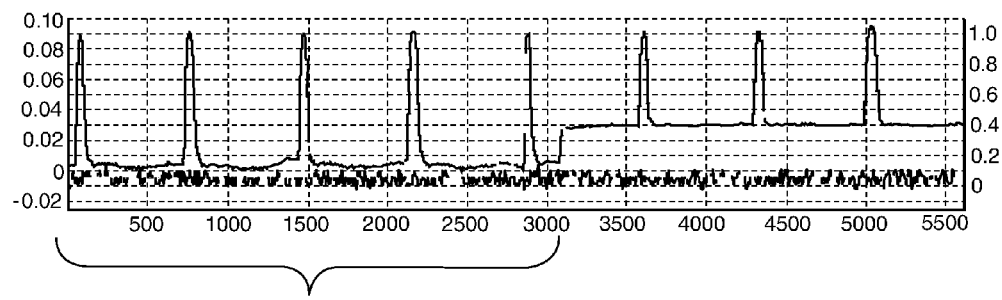
Figure 34:
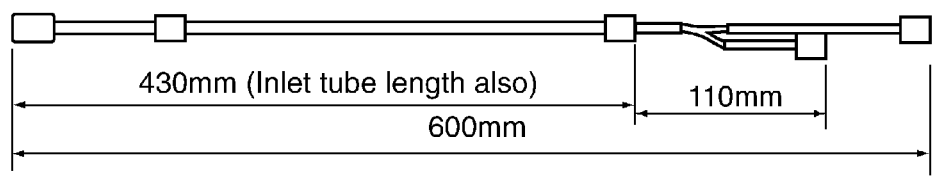
FIG. 34 shows an embodiment of an outlet tube for use in an embodiment of the invention.

Measurements were recorded while the pump motor is operating at 5 Vdc. The peak signal appears on average once every 700 ms: see FIG. 33. The peak signal level is the pump hose path and the base signal level is the tube set conductive path. During the pre-cycle count phase the first fluid sensor peaks only are included. The peak counter is the number of half turn pump rotations it will take to fill and empty the outlet tube. The number is rounded to four if the count is four or less and rounded down to five if the count is five or above. This may occur when a "Y" tube section is attached to the end of the outlet tube for dual channel endoscopes (FIG. 34). The peak counter snapshot time is set for 1 second, allowing for a 300 ms margin. Referring to FIG. 34 both the inlet and outlet tube are 430 mm in length, a combined length of 860 mm. With the Y hose outlet tube attached, the shortest route is 540 mm, and the longest length is 600 mm.

Measured Fluid Signal Levels from Six Pump Units

The following fluid sensor signal levels were measured. The values listed below are the decimal value measured by the micro ADC input pin. (ADC=mV/2)

PCA Sample 1 Pump Hose Tube Set
  Water (pre cycle) Peak=392 Tube set=100
  Disinfectant Peak=608 Tube set=236
  Water (post cycle) Peak=380 Tube set=120
PCA Sample 2
  Water (pre cycle) Peak=400 Tube set=100
  Disinfectant Peak=608 Tube set=236
  Water (post cycle) Peak=384 Tube set=112
PCA Sample 3
  Water (pre cycle) Peak=408 Tube set=104
  Disinfectant Peak=620 Tube set=236
  Water (post cycle) Peak=404 Tube set=108
PCA Sample 4
  Water (pre cycle) Peak=388 Tube set=108
  Disinfectant Peak=588 Tube set=228
  Water (post cycle) Peak=372 Tube set=104
PCA Sample 5
  Water (pre cycle) Peak=396 Tube set=108
  Disinfectant Peak=612 Tube set=236
  Water (post cycle) Peak=384 Tube set=108
PCA Sample 6
  Water (pre cycle) Peak=388 Tube set=108
  Disinfectant Peak=596 Tube set=288
  Water (post cycle) Peak=380 Tube set=108
  Average Levels
Water
  Pump hose Peak 389 (Min 380, Max 408) Tolerance±19 (5%) Min=380−10% (350)
  Tube Set Level 108 (Min 100, Max 120) Tolerance±12 (11%) Min=100−10% (90)
Hard Water
  Pump hose Peak 456 (Min 445, Max 478) Tolerance±22 (5%) Max=478+5% (500)
  Tube Set Level 160 (Min 148, Max 178) Tolerance±18 (11%) Max=178+10% (200)
Disinfectant (Soft Water)
  Pump hose Peak 605 (Min 588, Max 620) Tolerance±5 (2.5%) Min=588−10% (530)
  Tube Set Peak 243 (Min 228, Max 288) Tolerance±45 (19%) Min=228−10% (205)

Figure 35:
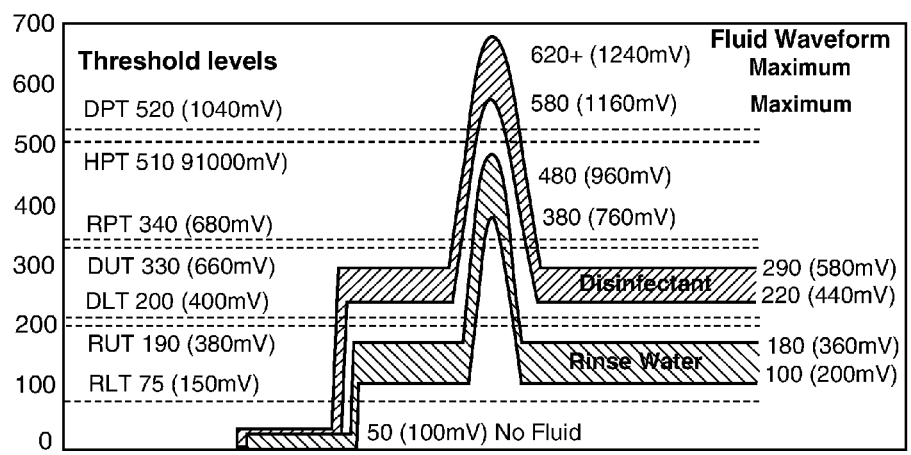
FIGS. 35-36 are graphs illustrating waveform and conductivity values for sterilant systems in accordance with aspects of the invention.
Figure 36:
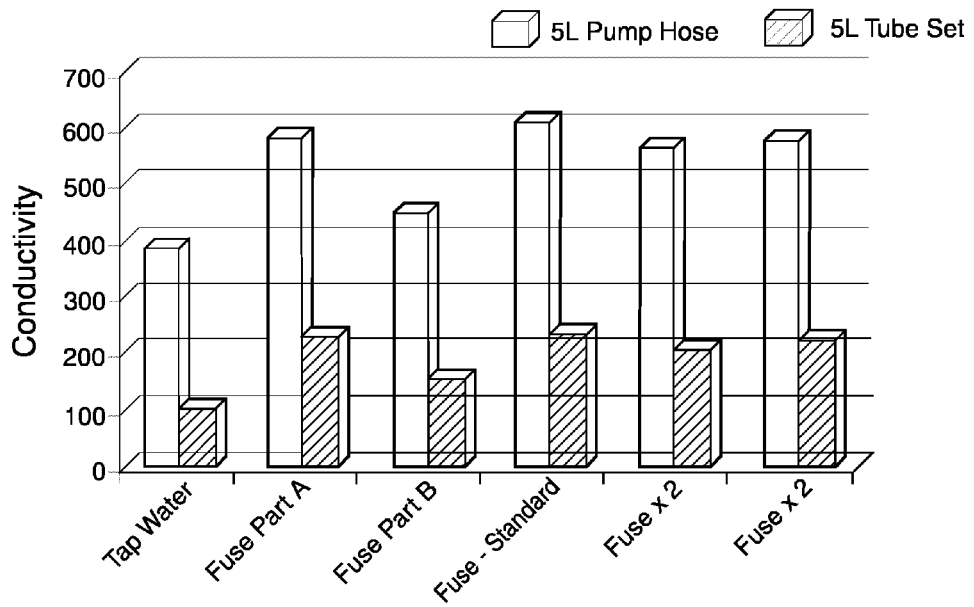

Results are shown in FIG. 35. Regardless of the hardness of the water, disinfectant threshold levels are distinguishable from rinse water threshold levels.

Sensor signal levels were tested for a two-part sterilant system (referred to herein as Fuse, which is a trade mark of Tristel PLC). The sterilant solution is prepared by mixing together Part A and Part B to produce a chlorine dioxide solution with a substantially greater concentration of sodium ions than tap water. Measurements were carried out on standard concentrations and on double concentrations which are used in some markets, and for differing water volumes. Results are given in Table 1 and graphed in FIG. 37.

The conductivity of the double concentrate was measured 5-7% lower than the standard concentration, a level of variation expected when comparing soft and hard tap water.

TABLE 1

| | Water Volume | | | | | |
|---|---|---|---|---|---|---|
| | 5 L | | 3.75 L | | 2.5 L | |
| | Pump Hose | Tube Set | Pump Hose | Tube Set | Pump Hose | Tube Set |
| Tap Water | 384 | 108 | 384 | 108 | 384 | 108 |
| Fuse Part A | 588 | 236 | 632 | 268 | 676 | 304 |
| Fuse Part B | 452 | 148 | 468 | 160 | 488 | 176 |
| Fuse Standard | 616 | 240 | 652 | 268 | 700 | 316 |
| Fuse x2 | 572 | 216 | 106% | 112% | 114% | 132% |
| Fuse x2 Variation from Standard | 584 −5%-7% | 228 −5%-10% | | | | |

From the results, we conclude that the conductive property of the double concentrate (used in China) is within the margin of variation when comparing hard and soft tap water (±10%). The Fuse concentration level would need to be much greater (>200%) before the operating performance of the pump unit could be affected. The conductive property of the standard Fuse disinfectant is the equivalent to the conductive property of the double concentrate (Fuse ×2) used in China. The firmware fluid sensor thresholds therefore can remain the same for both types of composition.

The invention has been described with reference to specific embodiments. It will be understood that various modifications may be made to the embodiments within the scope of the claims. For example, the peristaltic pump may be a linear pump or a rotary pump; the materials from which the hoses and fittings are made may be selected from any suitable materials that are resistant to the sterilising fluid with which they are to be used. The electronics and means for measuring electrical properties may be selected from arrangements well known per se to those skilled in the art of electronics. The various exemplary measurements, detection methodologies, and modes of operation may be varied in accordance with specific needs and specific apparatus design and disinfectant materials.

The invention claimed is:

1. A peristaltic pump for use in sterilising a lumen of an endoscope in a sterilisation compartment of a sterilisation apparatus, the pump comprising:
    a flexible pump hose having an outlet end and an inlet end, and an electrically conductive fitting at each end in contact with fluid in the pump hose;
    a motor-driven impeller disposed in relation to the pump hose such that when the impeller is driven it will intermittently bear against the pump hose so as to bring the internal walls of the pump hose together;
    a first electrode in contact with the conductive fitting at the outlet end of the pump hose, and a second electrode in contact with the conductive fitting at the inlet end of the pump hose;
    circuitry for applying a voltage across the first and second electrodes; and
    circuitry for measuring an electrical property between the conductive fittings;
    wherein when the outlet end of the pump hose is connected to one end of the endoscope having the lumen to be sterilised and immersed in a conductive sterilant liquid in the sterilisation compartment, and the inlet end of the pump hose is in connection with the sterilant liquid in the sterilisation compartment, the only conductive path that will exist between the first electrode and the second electrode when the pump is operated, apart from via the pump hose, will be via the lumen of the endoscope.

2. The pump according to claim 1, wherein the impeller is mounted for rotary motion and wherein when the impeller is rotated at least one point exists at which the pump hose is incompletely occluded so that a fluid path exists through the pump hose from the inlet end to the outlet end.

3. The pump according to claim 1, wherein the impeller is arranged and adapted intermittently to bring the internal walls of the pump hose together to make a substantially fluid-tight seal.

4. The pump according to claim 1, further comprising circuitry for signalling an error condition if the measured electrical property is outside a specified value range.

5. The pump according to claim 1, further comprising circuitry for measuring a load current of the motor and circuitry for determining whether a blockage is present depending on the measured load current.

6. The pump according to claim 1, further comprising an outlet hose for connecting the outlet end of the pump hose to the endoscope to be sterilised; wherein the outlet hose is in two parts connected together by an electrically conductive connector.

7. The pump according to claim 1, further comprising an inlet hose connected to the inlet end of the pump hose, for immersion in a source of sterilant liquid; the inlet hose being provided with an electrically conductive fitting at its free end.

8. A sterilisation apparatus comprising a container having the sterilisation compartment for receiving the endoscope to be sterilised, and the peristaltic pump as claimed in claim 1, for pumping the sterilant liquid to and from the sterilisation compartment.

9. The apparatus according to claim 8, further comprising an electronic controller for operating a drainage valve to allow fluid to drain from the sterilisation compartment after a predetermined time period; the controller being linked to the pump in a manner which permits the controller to control one or more operating modes of the pump.

10. The apparatus according to claim 9, wherein the controller is arranged and adapted to receive data from the pump.

11. A method of using the apparatus of claim 8 for sterilising the endoscope having the lumen, the method including the steps of:
    placing the endoscope in the sterilisation compartment;
    connecting the outlet end of the pump hose to the one end of the endoscope to establish a fluid connection between the pump hose and the lumen;
    filling the sterilisation compartment with the sterilant liquid;
    providing the inlet end of the pump hose with an inlet hose, and disposing the free end of the inlet hose in the sterilant liquid within the sterilisation compartment;
    operating the pump so that the impeller causes fluid to be pumped through the lumen of the endoscope and causes fluid to be drawn into the free end of the inlet hose; and
    measuring the electric property between the conductive fittings of the pump hose.

12. The method according to claim 11, further comprising the steps of:
    comparing the measured electrical property with a predetermined value range; and
    signalling an error condition if the measured property is outside the value range.

13. The method according to claim 11 further comprising measuring a load current of the motor and determining from the measured value whether:
    (i) the pump is operating normally, or
    (ii) a blockage is present within the endoscope or one of the hoses; or
    (iii) the motor has stalled.

14. The method according to claim 13, further comprising triggering an alarm or error signal if the blockage is detected or if the motor has stalled.

15. The method according to claim 11,
    wherein the outlet end of the pump hose is connected to the endoscope via a Luer connection which is electrically conductive, and wherein the free end of the inlet hose is provided with a strainer to filter particulates from fluid entering the inlet hose.

* * * * *